US008148084B2

(12) United States Patent
O'Connor et al.

(10) Patent No.: US 8,148,084 B2
(45) Date of Patent: Apr. 3, 2012

(54) DIAGNOSIS OF AUTOIMMUNE DISEASE

(75) Inventors: Kevin C. O'Connor, Braintree, MA (US); David A. Hafler, Newton, MA (US); Kai W. Wucherpfennig, Brookline, MA (US); Katherine McLaughlin, Watertown, MA (US); William H. Robinson, Palo Alto, CA (US); Lawrence Steinman, Stanford, CA (US)

(73) Assignees: Dana-Farber Cancer Institute, Inc., Boston, MA (US); Brigham and Women's Hospital, Inc., Boston, MA (US); The Trustees of the Leland Stanford Junior University, Palo Alto, CA (US); Department of Veterans Affairs, Washington, DC (US)

( * ) Notice: Subject to any disclaimer, the term of this patent is extended or adjusted under 35 U.S.C. 154(b) by 443 days.

(21) Appl. No.: 11/766,608

(22) Filed: Jun. 21, 2007

(65) Prior Publication Data

US 2009/0054251 A1     Feb. 26, 2009

Related U.S. Application Data

(60) Provisional application No. 60/815,698, filed on Jun. 22, 2006.

(51) Int. Cl.
*G01N 33/53* (2006.01)
(52) U.S. Cl. .......................................... 435/7.1; 435/7.5
(58) Field of Classification Search .................... None
See application file for complete search history.

(56) References Cited

U.S. PATENT DOCUMENTS

| 2004/0143094 A1 | 7/2004 | Donda et al. |
| 2005/0009096 A1 | 1/2005 | Genain et al. |

OTHER PUBLICATIONS

Vallbracht, I., et al. Ann. Rheum. Dis. 2004;63:1079-1084.*
Barker, J.M., et al. J. Clin. Endocrinol. 2004;89:3896-3902.*
Menge, T., et al. Eur. J. Immunol. 2007;37:3229-3239.*
Berger et al., N. Engl. J. Med. 349(2):139-45 (2003).
Bettadapura et al., J. Neurochem. 70(4):1593-1599 (1998).
Brass et al., Pediatr. Neurol. 29(3):227-31 (2003).
Brehm et al., J. Neuroimmunol. 97(12):9-15 (1999).
Breithaupt et al., Proc. Natl. Acad. Sci. U. S. A., 100(16):9446-51 (2003).
Falk et al., J. Exp. Med. 191(4):717-730 (2000).
Fossati-Jimack et al., J. Exp. Med., 190(11):1689-96 (1999).
Gaertner et al., Neurology 63(12):2381-3 (2004).
Garg, Postgrad. Med. J. 79:11-17 (2003).
Genain et al., J. Clin. Invest.96(6):2966-74 (1995).
Genain et al., Nat. Med. 5(2):170-5 (1999).
Hart et al., J. Neuroimmunol. 163(1-2):31-39 (2005).
Hashimoto et al., J. Rheumatol. 18(4):545-51 (1991).
Hjelmstrom et al., J. Immunol. 161(9):4480-3 (1998).
Jaquet et al., Mol. Brain Res. 43(1-2):333-337 (1996).
Kennedy, J. Neurol. 252(3):268-72 (2005).
Khurana et al., Pediatrics 116(2):431-6 (2005).
LaGasse et al., Diabetes Care 25(3):505-11 (2002).
Lalive et al., Proc. Natl. Acad. Sci. U. S. A. 103(7):2280-5 (2006).
Lampasona et al., Neurology 62(11):2092-4 (2004).
Legge et al., J. Exp. Med. 196(2):217-227 (2002).
Lim et al., Multiple Sclerosis 11(4):492-4 (2005).
Lindert et al., Brain 122 (Pt 11):2089-2099 (1999).
Linington et al., Am. J. Pathol. 130(3):443-54 (1988).
Lisak et al., Neurology 24(6):560-4 (1974).
Mathey et al., Eur. J. Immunol. 34(8):2065-71 (2004).
McDonald et al., Ann. Neurol. 50(1):121-7 (2001).
Menge et al., Arch. Neurol. 62(11):1673-80 (2005).
O'Connor et al., J. Immunol. 136:140-148 (2003).
O'Connor et al., J. Immunol. 175(3):1974-82 (2005).
O'Connor et al., Neurology 64(6):A417 Supplement 1 (2005).
O'Connor et al., Nature Medicine:1-7 (2007).
Pohl-Koppe et al., J. Neuroimmunol. 91(1-2):19-27 (1998).
Polman et al., Ann. Neurol. 58:840-846 (2005).
Reindl et al., Brain 122 (Pt 11):2047-56 (1999).
Robinson et al., Nat. Biotechnol. 21(9):1033-9 (2003).
Robinson et al., Nature Medicine 8:295-301 (2002).
Rust, Semin. Pediatr. Neurol. 7(2):66-90 (2000).
Schluesener et al., J. Immunol. 139(12):4016-21 (1987).
Solly et al., J. Neurochem. 68(4):1705-1711 (1997).
von Budingen et al., Eur. J. Immunol. 34(8):2072-83 (2004).
Warren et al., Proc. Natl. Acad. Sci. U. S. A. 92(24):11061-5 (1995).
Wegner, Int. MS J. 12(1):13-9 (2005).
Zocher et al., International Immunology 15(7):789-796 (2003).
Zocher et al., Mol. Immunol. 41(5):511-518 (2004).
Khalil et al., J. Neuroimmunolol. 70: 147-156 (2006).

* cited by examiner

*Primary Examiner* — Gerald R Ewoldt
(74) *Attorney, Agent, or Firm* — Fish & Richardson P.C.

(57) ABSTRACT

Methods and compositions for diagnosing and treating autoimmune disease, e.g., acute disseminated encephalomyelitis (ADEM), are described.

15 Claims, 12 Drawing Sheets

```
1    AAGCTTGCCGCCACCATGGTACCGTGCACGCTGCTCCTGCTGTTGGCGGCCGCCCTGGCT
1                   M  V  P  C  T  L  L  L  L  A  A  A  L  A    leader 61   CCGACTCAGACCCGCGCGCAGTTCAGAGTGATAGGACCAAGACACCCTATCCGGGCTCTG
21    P  T  Q  T  R  A  Q  F  R  V  I  G  P  R  H  P  I  R  A  L  MOG EC 121  GTCGGGGATGAAGTGGAATTGCCATGTCGCATATCTCCTGGGAAGAACGCTACAGGCATG
41    V  G  D  E  V  E  L  P  C  R  I  S  P  G  K  N  A  T  G  M 181  GAGGTGGGGTGGTACCGCCCCCCCTTCTCTAGGGTGGTTCATCTCTACAGAAATGGCAAG
61    E  V  G  W  Y  R  P  P  F  S  R  V  V  H  L  Y  R  N  G  K 241  GACCAAGATGGAGACCAGGCACCTGAATATCGGGGCCGGACAGAGCTGCTGAAAGATGCT
81    D  Q  D  G  D  Q  A  P  E  Y  R  G  R  T  E  L  L  K  D  A 301  ATTGGTGAGGGAAAGGTGACTCTCAGGATCCGGAATGTAAGGTTCTCAGATGAAGGAGGT
101   I  G  E  G  K  V  T  L  R  I  R  N  V  R  F  S  D  E  G  G 361  TTCACCTGCTTCTTCCGAGATCATTCTTACCAAGAGGAGGCAGCAATGGAATTGAAAGTA
121   F  T  C  F  F  R  D  H  S  Y  Q  E  E  A  A  M  E  L  K  V 421  GAAGATCCTTTCTACTGGGGATCCGGCATGGGCATGGGCATGGGCATGATGGCGGAAGCG
141   E  D  P  F  Y  W  G  S  G  M  G  M  G  M  G  M  M  A  E  A   linker, SA 481  GGCATCACCGGCACCTGGTATAACCAGCTGGGCAGCACCTTCATCGTGACCGCGGGCGCG
161   G  I  T  G  T  W  Y  N  Q  L  G  S  T  F  I  V  T  A  G  A 541  GATGGCGCGCTGACCGGCACCTATGAAAGCGCGGTGGGCAACGCGGAAAGCCGCTATGTG
181   D  G  A  L  T  G  T  Y  E  S  A  V  G  N  A  E  S  R  Y  V 601  CTGACCGGCCGCTATGATAGCGCGCCGGCGACCGATGGCAGCGGTACCGCGCTGGGCTGG
201   L  T  G  R  Y  D  S  A  P  A  T  D  G  S  G  T  A  L  G  W 661  ACCGTGGCGTGGAAAAACAACTATCGCAACGCGCATAGCGCGACCACCTGGAGCGGCCAG
221   T  V  A  W  K  N  N  Y  R  N  A  H  S  A  T  T  W  S  G  Q 721  TATGTGGGCGGCGCGGAAGCGCGCATCAACACCCAGTGGCTGCTGACCAGCGGCACCACC
241   Y  V  G  G  A  E  A  R  I  N  T  Q  W  L  L  T  S  G  T  T 781  GAAGCGAACGCGTGGAAAAGCACCCTGGTGGGCCATGATACCTTCACCAAAGTGAAACCG
261   E  A  N  A  W  K  S  T  L  V  G  H  D  T  F  T  K  V  K  P 841  AGCGCGGCGAGCTGAAAAAAAAAAAAAAAAAAAAAAAGCTT    (SEQ ID NO:1)
281   S  A  A  S  *                               (SEQ ID NO:2)
```

FIG. 5

```
  1 AAGCTTGCCGCCACCATGGTACCGTGCACGCTGCTCCTGCTGTTGGCGGCCGCCCTGGCT    HindIII
  1                 M  V  P  C  T  L  L  L  L  A  A  A  L          K^b Leader 61 CCGACTCAGACCCGCGCGGCGGAAGCGGGCATCACCGGCACCTGGTATAACCAGCTGGGC
 21  P  T  Q  T  R  A  A  E  A  G  I  T  G  T  W  Y  N  Q  L  G     SA 121 AGCACCTTCATCGTGACCGCGGGCGCGGATGGCGCGCTGACCGGCACCTATGAAAGCGCG
 41  S  T  F  I  V  T  A  G  A  D  G  A  L  T  G  T  Y  E  S  A 181 GTGGGCAACGCGGAAAGCCGCTATGTGCTGACCGGCCGCTATGATAGCGCGCCGGCGACC
 61  V  G  N  A  E  S  R  Y  V  L  T  G  R  Y  D  S  A  P  A  T 241 GATGGCAGCGGTACCGCGCTGGGCTGGACCGTGGCGTGGAAAAACAACTATCGCAACGCG
 81  D  G  S  G  T  A  L  G  W  T  V  A  W  K  N  N  Y  R  N  A 301 CATAGCGCGACCACCTGGAGCGGCCAGTATGTGGGCGGCGCGGAAGCGCGCATCAACACC
101  H  S  A  T  T  W  S  G  Q  Y  V  G  G  A  E  A  R  I  N  T 361 CAGTGGCTGCTGACCAGCGGCACCACCGAAGCGAACGCGTGGAAAAGCACCCTGGTGGGC
121  Q  W  L  L  T  S  G  T  T  E  A  N  A  W  K  S  T  L  V  G 421 CATGATACCTTCACCAAAGTGAAACCGAGCGCGGCGAGCGGATCCGGCATGGGCATGGGC    BamHI
141  H  D  T  F  T  K  V  K  P  S  A  A  S  G  S  G  M  G  M  G     Linker 481 ATGGGCATGATGGGCGGCGGACAGTTCAGAGTGATAGGACCAAGACACCCTATCCGGGCT
161  M  G  M  M  G  G  G  Q  F  R  V  I  G  P  R  H  P  I  R  A     MOG EC 541 CTGGTCGGGGATGAAGTGGAATTGCCATGTCGCATATCTCCTGGGAAGAACGCTACAGGC
181  L  V  G  D  E  V  E  L  P  C  R  I  S  P  G  K  N  A  T  G 601 ATGGAGGTGGGGTGGTACCGCCCCCCCTTCTCTAGGGTGGTTCATCTCTACAGAAATGGC
201  M  E  V  G  W  Y  R  P  P  F  S  R  V  V  H  L  Y  R  N  G 661 AAGGACCAAGATGGAGACCAGGCACCTGAATATCGGGGCCGGACAGAGCTGCTGAAAGAT
221  K  D  Q  D  G  D  Q  A  P  E  Y  R  G  R  T  E  L  L  K  D 721 GCTATTGGTGAGGGAAAGGTGACTCTCAGGATCCGGAATGTAAGGTTCTCAGATGAAGGA
241  A  I  G  E  G  K  V  T  L  R  I  R  N  V  R  F  S  D  E  G 781 GGTTTCACCTGCTTCTTCCGAGATCATTCTTACCAAGAGGAGGCAGCAATGGAATTGAAA
261  G  F  T  C  F  F  R  D  H  S  Y  Q  E  E  A  A  M  E  L  K 841 GTAGAAGATCCTTTCTACTGGTGAAAAAAAAAAAAAAAAAAAAAAGCTT    HindIII  (SEQ ID NO:3)
281  V  E  D  P  F  Y  W  *                                        (SEQ ID NO:4)
```

FIG. 6

```
1    AAGCTTGCCGCCACCATGGTACCGTGCAGCTGCTCCTGCTGTTGGCGGCCCCTGGCT    HindIII
1                  M  V  P  C  T  L  L  L  L  A  A  A  L  A     K^b Leader 61   CCGACTCAGACCCGCGCCCAGTTCAGAGTTGATAGGACCAAGACCACCCTATCCGGGCTCTG
21    P  T  Q  T  R  A  Q  F  R  V  I  G  P  R  H  P  I  R  A  L    MOG ec domain 121  GTCGGGGATGAAGTGGAATTGCCATGTCGCATATCTCCTGGAAGAACGCTACAGGCATG
41    V  G  D  E  V  E  L  P  C  R  I  S  P  G  K  N  A  T  G  M 181  GAGGTGGGGTGGTACCGCCCCCCCTTCTCTAGGGTGGTTCATCTCTACAGAAATGGCAAG
61    E  V  G  W  Y  R  P  P  F  S  R  V  V  H  L  Y  R  N  G  K 241  GACCAAGATGGAGACCAGGCACCTGAATATCGGGGCCGACAGAGCTGCTGAAAGATGCT
81    D  Q  D  G  D  Q  A  P  E  Y  R  G  R  T  E  L  L  K  D  A 301  ATTGGTGAGGGAAAGGTGACTCTCCGAGATCATTCTTACCAAGAGGAGCAATTGAAAGTA
101   I  G  E  G  K  V  T  L  R  I  R  N  V  R  F  S  D  E  G  G 361  TTCACCTGCTTCTTCCGAGATCATTCTTACCAAGAGGAGGCAGCAATGGAATTGAAAGTA
121   F  T  C  F  F  R  D  H  S  Y  Q  E  E  A  A  M  E  L  K  V 421  GAAGATCCTTTCTACTGGGGATCCGGCATGGGCATGGGGATGATGTGAAAAAAA
141   E  D  P  F  Y  W  G  S  G  M  G  M  G  M  G  M  M  *    "Linker" (SEQ ID NO:5)

481  AAAAAAAAAAAAAAAGCTT                                          HindIII  (SEQ ID NO:6)
```

FIG. 7

DIAGNOSIS OF AUTOIMMUNE DISEASE

CLAIM OF PRIORITY

This application claims the benefit under 35 USC §119(e) of U.S. Provisional Patent Application Ser. No. 60/815,698, filed on Jun. 22, 2006, the entire contents of which are hereby incorporated by reference.

FEDERALLY SPONSORED RESEARCH OR DEVELOPMENT

This invention was made with Government support under Grant Nos. NS24247, R01 AI39229, R01 AI44447, P01 AI045757, RO1 NS41402-01A1, and KO8 AR02133-02, awarded by the National Institutes of Health. The Government has certain rights in the invention.

TECHNICAL FIELD

This invention relates to methods and compositions for the diagnosis of autoimmune disease.

BACKGROUND

The role of autoantibodies in the pathogenesis of human demyelinating diseases of the central nervous system (CNS) is an important unresolved issue in the field of neuroimmunology. In animal models, autoantibodies that recognize epitopes located on the surface of myelin or myelin-producing oligodendrocytes can enhance demyelination (Linington et al., Am. J. Pathol., 1988, 130(3):443-54; Schluesener et al., J. Immunol., 1987, 139(12):4016-21).

Injection of a monoclonal antibody (mAb 8-18C5) against myelin oligodendrocyte glycoprotein (MOG) into mice or rats with mild experimental autoimmune encephalomyelitis (EAE) induces severe demyelination, but does not induce any disease in healthy animals because the antibody does not gain access to the CNS parenchyma (Linington et al., Am. J. Pathol. 1988; 130(3):443-54; Schluesener et al., J. Immunol. 1987; 139(12):4016-21). MOG is a relatively minor protein component of myelin, but is localized on the outer surface of the multi-lamellar myelin structure, while more abundant antigens such as myelin basic protein (MBP) are inaccessible to antibodies in intact myelin (Linington et al., Am. J. Pathol. 1988; 130(3):443-54).

In the marmoset primate model of EAE, immunization with MOG induces a chronic demyelinating disease with pathological features reminiscent of multiple sclerosis (MS) (Genain et al., J. Clin. Invest. 1995; 96(6):2966-74). However, in mouse models, severe demyelination is observed even in the apparent absence of antibodies and B cells (Hjelmstrom et al., J. Immunol. 1998; 161(9):4480-3), indicating that autoantibodies are not required for demyelination in all species.

These studies in animal models have demonstrated the demyelinating potential of autoantibodies to myelin surface proteins, but their role in the pathogenesis of human diseases is far less certain. Multiple sclerosis (MS) and acute disseminated encephalomyelitis (ADEM) are the most common demyelinating diseases in adults and children, respectively.

SUMMARY

The present invention is based, at least in part, on the development of novel approaches for the identification and detection of autoantibodies that can be used to investigate their role in the pathogenesis of human demyelinating CNS diseases. The methods described herein are useful for diagnosing a subject with acute disseminated encephalomyelitis (ADEM), e.g., ruling out a diagnosis of multiple sclerosis (MS) or viral encephalitis, by detecting the presence of anti-MOG antibodies in the serum or CSF of a subject, e.g., using the tetrameric antigens described herein. In addition, the methods described herein can be used to diagnose a subject with ADEM, e.g., to rule out a diagnosis of MS or viral encephalitis, e.g., by detecting the presence of anti-MOG antibodies, anti-myelin-associated oligodendrocyte basic protein (MOBP) antibodies, and anti-MBP antibodies in the serum or CSF of a subject, e.g., using an array.

Thus, in one aspect, the invention provides polypeptides including a first portion including an antigen of interest, e.g., an antigen selected from myelin oligodendrocyte glycoprotein (MOG), myelin basic protein (MBP), and Cluster of Differentiation 2 (CD2), or an antigenic fragment thereof, e.g., the extracellular domain of a transmembrane protein such as MOG or CD2; and a second portion including multimerizing domain, e.g., streptavidin, linked to the first portion, optionally via a linker, e.g., a flexible linker. Multimerized polypeptides, e.g., tetrameric polypeptides including four of these polypeptides, are also within the scope of the present invention.

In another aspect, the invention provides methods for diagnosing a subject for possible autoimmune diseases. The methods include obtaining a sample including serum or CSF from the subject; contacting the sample with a multimeric antigen, e.g., a tetrameric polypeptide as described herein, under conditions that allow binding of the tetrameric polypeptide to antibodies present in the sample, if any, to form tetrameric polypeptide/antibody complexes; and detecting the presence of tetrameric polypeptide/antibody complexes in the sample. The presence of tetrameric polypeptide/antibody complexes indicates that the subject has an autoimmune disease.

In some embodiments, the polypeptides include MOG or an antigenic fragment thereof, and the autoimmune disease is ADEM.

In a further aspect, the invention features methods for differentially diagnosing a subject suspected of having MS or ADEM, by detecting the presence of MOG autoantibodies in the serum or CSF of the subject using a method described herein, wherein the presence of MOG autoantibodies indicates that the subject has ADEM and not MS.

In some embodiments, the methods described herein include detecting autoantibodies that only bind to folded antigens, e.g., selectively bind to antigens that are in its native three-dimensional form, and do not substantially bind to denatured antigen.

In another aspect, the invention provides methods for treating a subject with an autoimmune disease. The methods include performing plasmapheresis on the blood of the subject using a tetrameric polypeptide as described herein, e.g., on a subject diagnosed with ADEM, e.g., by a method described herein.

In yet another aspect, the invention provides methods for selecting or rejecting a subject for inclusion in a clinical trial. The methods include detecting the presence of MOG autoantibodies in a sample including serum or CSF of the subject, e.g., by a method described herein, and selecting or rejecting the subject for inclusion in the trial based upon the presence or absence of MOG autoantibodies in the sample.

In still another aspect, the invention provides methods for detecting the presence of an antibody to a selected antigen in a sample, e.g., a low-affinity antibody. The methods include contacting the sample with a tetrameric polypeptide including the selected antigen, under conditions that allow binding of the tetrameric polypeptide to antibodies present in the sample, if any, to form tetrameric polypeptide/antibody complexes; and detecting the presence of tetrameric polypeptide/ antibody complexes in the sample, thereby detecting the presence of the antibody in the sample.

In a further aspect, the invention features methods for diagnosing a subject with ADEM, by detecting the presence of anti-MOG antibodies and/or anti-MBP antibodies in a sample including blood or CSF from the subject, wherein the presence of anti-MOG and/or anti-MBP antibodies in the sample indicates that the subject has ADEM. In some embodiments, the methods include detecting the presence of anti-MOG antibodies. In some embodiments, the ADEM is referred to as anti-MOG associated ADEM.

In an additional aspect, the invention provides methods for diagnosing a subject with ADEM. The methods include obtaining a sample including serum or CSF from the subject; contacting the sample with antigens comprising:
  (i) all or an antigenic fragment of MOG;
  (ii) all or an antigenic fragment of MBP; and
  (iii) all or an antigenic fragment of MOBP;
under conditions that allow binding of the antigens to antibodies present in the sample, if any, to form MOG antigen/ antibody complexes, MBP antigen/antibody complexes, and MOBP antigen/antibody complexes; and detecting the presence of the MOG antigen/antibody complexes, MBP antigen/ antibody complexes, and MOBP antigen/antibody complexes in the sample. The presence of MOG antigen/antibody complexes, MBP antigen/antibody complexes, and MOBP antigen/antibody complexes indicates that the subject has ADEM.

In some embodiments, the methods include contacting the sample with any four or more antigenic protein fragments selected from the group of hMBP 80-102, rMBP 10-20, MBP 9-20 Ac, hMOBP15-36, hMOBP 51-70, MBP 85-99, rMOG 7-24, MOG P15, rMOG 25-42, mMOG 79-96, hMBP 20-28, hMBP 29-37, and hMBP 1-20, under conditions that allow binding of the antigens to antibodies present in the sample, if any, to form antigen/antibody complexes; and detecting the presence of antigen/antibody complexes in the sample; the presence of antigen/antibody complexes indicates that the subject has ADEM. In some embodiments, the antigenic protein fragments are labeled.

In some embodiments, the methods include contacting the sample with all of the antigenic protein fragments listed in Table 4. In some embodiments, the antigenic protein fragments are immobilized on a substrate, e.g., in a protein array. In some embodiments, the methods include contacting the sample to a protein array including the selected antigenic protein fragments.

In some embodiments, the methods include detecting, in serum or CSF from the subject, the presence of autoantibodies that bind to
  (i) at least one antigenic protein fragment selected from the group consisting of hMBP 80-102, rMBP 10-20, MBP 85-99, MBP 9-20 Ac, hMBP 20-28, hMBP 29-37, and hMBP 1-20;
  (ii) at least one antigenic protein fragment selected from the group consisting of hMOBP15-36 and hMOBP 51-70, and
  (iii) at least one antigenic protein fragment selected from the group consisting of rMOG 7-24, MOG P15, rMOG 25-42, mMOG 79-96.
The presence of the autoantibodies indicates that the subject has ADEM.

In some embodiments, the subject is Caucasian.

Epitopes are portions of antigens that are recognized by antibodies or T cell antigen receptors. An individual antigen typically contains multiple epitopes, although there are instances in which an antigen contains a single epitope. In one embodiment of this invention, peptide fragments derived from a whole protein antigen are used to represent individual epitope(s) targeted by the antibodies produced by B cells.

In another embodiment, portions of molecules including post-translational modifications, carbohydrates, lipids and other molecules can be used to represent individual epitopes. Epitopes are shapes recognized by immune B and T cells, and can be mimicked by non-antigen derived peptides and other molecules that possess the same shape as the epitope that is present within the native antigen. An example of an element with an epitope shape is an aptamer. An aptamer is a molecule that provides a shape that can be designed or selected to mimic an immunologic epitope. Using a plurality of aptamers, a library of epitope shapes can be generated. Where peptides are used as an epitope to detect antibody binding, peptides will usually be at least about 7 amino acids in length, at least about 15 amino acids in length, and as many as 22 or more amino acids in length. The optimal epitopes can be identified by using overlapping peptide fragments of a target protein. The fragments can be overlapping by, for example, 7-10 amino acids, and can encompass the whole sequence of a protein of interest or just a portion thereof, e.g., the extracellular domain of a membrane protein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 5 is the nucleotide (SEQ ID NO:1) and amino acid (SEQ ID NO:2) sequences of the MOG-SA construct.

FIG. 6 is the nucleotide (SEQ ID NO:3) and amino acid (SEQ ID NO:4) sequences of the SA-MOG construct.

FIG. 7 is the nucleotide (SEQ ID NO:5) and amino acid (SEQ ID NO:6) sequences of the MOG monomer construct.

DETAILED DESCRIPTION

Figure 1A:
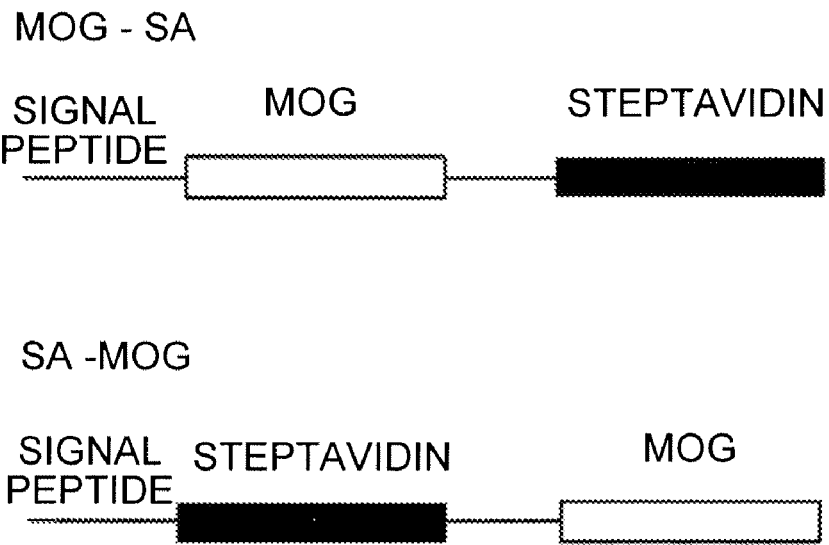
FIG. 1A is a schematic drawing illustrating the design of antigen-streptavidin (SA) fusion proteins. The extracellular Ig domain of MOG was connected to the N-terminus (MOG-SA) or C-terminus (SA-MOG) of the SA monomer via a flexible linker.

Described herein are a number of methods for diagnosing autoimmune diseases by detecting the presence of autoantibodies that bind to native epitopes. The multimeric antigens described herein can be used to diagnose a subject with an autoimmune disease, e.g., a neurological autoimmune disease, that is characterized by the presence of low-affinity autoantibodies. In some embodiments, the autoimmune disease is ADEM, but the methods described herein, e.g., using tetrameric antigens, can also be used to demonstrate the presence of autoantibodies associated with other autoimmune diseases, as discussed below.

The results described herein demonstrate the presence of circulating autoantibodies to myelin surface antigens in patients with ADEM. In contrast, MOG autoantibodies were identified only in rare cases of MS. Thus, the compositions and methods described herein allow for the differential diagnosis of MS and anti-MOG-associated forms of ADEM, and permit identification of a subset of ADEM patients with evidence for antibody-mediated autoimmunity that help in the selection and optimization of treatment options.

The methods described herein also facilitate the differential diagnosis of ADEM and viral encephalitis by permitting positive identification of patients with an autoimmune response. In the acute clinical setting, rapid differentiation of ADEM and viral encephalitis is important because of the different modes of treatment (Kennedy, J. Neurol., 2005, 252(3):268-72).

As one example, MOG multimeric antigens can be used in assays to detect the presence of anti-MOG autoantibodies, to thereby diagnose ADEM, to confirm a diagnosis of ADEM, and to differentially diagnose a subject with ADEM versus MS.

In some embodiments, the methods will include identifying a subject who is suspected of having an autoimmune disease, e.g., suspected of having ADEM, or suspected of having ADEM or MS. Such subjects can be identified by the presence of certain clinical features (e.g., headache, meningismus, and altered mental status with confusion progressing to lethargy and coma; cranial nerve involvement, e.g., optic neuritis; motor involvement, e.g., ranging from focal spastic weakness to quadriplegia; sensory findings; evidence of transverse myelitis; and/or cerebellar dysfunction), MRI findings (e.g., patchy areas of increased signal intensity), and pathogenesis (e.g., perivascular infiltrates of lymphocytes, macrophages and/or monocytes, perivascular demyelination, and/or axonal damage). The methods may also include obtaining a sample from a subject. Samples will usually include cerebrospinal fluid (CSF) or serum.

Samples from such subjects are then contacted with the multimeric antigens described herein, for a sufficient amount of time and under conditions that allow formation of complexes between the multimeric antibodies and any autoantibodies in the sample. Then the presence of any complexes is detected and, in some embodiments, quantified.

The presence of the complexes can be detected using assays known in the art. For example, the multimeric antigen may be labeled, e.g., using a detectable label such as a radiolabel or fluorescent label, and the labeled complexes may be detected. Alternatively or in addition, the complex can be detected based on molecular weight. Optionally, the complexes can be isolated from the sample, e.g., by incubation with Protein A-Sepharose, or another moiety appropriate for the multimerization domain.

Thus, the methods described herein can be used to detect the presence of an autoantibody in the subject, e.g., in the serum or CSF of the subject.

Multimeric Antigens

Described herein are multimeric antigens that include auto-antigen domains and multimerization domains. Examples include tetrameric streptavidin antigen polypeptides and polynucleotides encoding them. In some embodiments, the tetrameric antigens include streptavidin and an antigen, e.g., an autoantigen.

Autoantibodies

Autoantibodies are a hallmark of, and represent a component of the diagnostic criteria for, certain autoimmune diseases, such as systemic lupus erythematosus and rheumatoid arthritis. In autoimmune diabetes and rheumatoid arthritis, detection of autoantibodies targeting multiple autoantigens provides greater diagnostic value than detection of antibodies against individual epitopes (Verge et al., Diabetes, 1996, 45:926-33; Schellekens et al., Arthritis Rheum., 2000, 43(1): 155-63). With the advent of protein array technologies (Robinson et al., Nature Medicine, 2002, 8:295-301), it is now possible to survey the specificity of autoantibody responses in clinical samples against hundreds or thousands of peptides and proteins. Studies applying protein arrays to profile autoantibody responses in rodent models of multiple sclerosis suggest that detection of autoantibodies targeting epitopes represented by both native proteins and linear peptides provides increased utility for assessing prognosis in this model of autoimmune demyelinating disease (Robinson et al., Nature Biotechnol., 2003, 21:1033-9).

Auto-Antigen Domains

Suitable autoantigens include, e.g., autoantigens that are recognized by low-affinity antibodies that may be associated with an autoimmune disease. Table 1 lists exemplary diseases and their known or suspected autoantigen, the presence of which may be detected using an appropriate multimeric autoantigen.

TABLE 1

Autoimmune diseases and known or suspected autoantigens

| Disease | Putative Autoantigen |
|---|---|
| Stiff Person Syndrome (SPS) | GAD |
| Multiple Sclerosis | myelin proteins (e.g., proteolipid protein (PLP) and/or MBP) |
| autoimmune inner ear disease | Myelin protein Po |
| acute inflammatory demyelinating polyradiculoneuropathy | peripheral nerve myelin protein-22 (PMP22) |
| Myasthenia Gravis | Gravin, Titin |
| Systemic Lupus Erythematosus | RNA polymerase I, RNA-binding protein Ro, nucleolin |
| Rheumatoid Arthritis | citrullinated fibrinogen, citrullinated α-enolase |
| Type I diabetes | Insulin |
| Thyroiditis | Thyroglobulin |
| Lupus SLE | DNA |

As one example, myelin proteins such as Myelin Basic Protein (MBP), MOG, $P_0$ Protein, Connexin-32 protein, Myelin-Associated Glycoprotein (MAG), P2 basic protein, 170 kDa glycoprotein (SAG), Schwann cell myelin protein (SMP), Oligodendrocyte-myelin glycoprotein (OMgp), and peripheral nerve myelin protein-22 (PMP22) can be used. Useful controls include T-cell differentiation antigen cluster 2 (CD2). Other antigens can also be used, e.g., other cell-surface antigens such as the NMDA receptor (NMDA-R), and Aquaporin-4, as well as those antigens listed in Table 1, above. Where the cell-surface antigen is a membrane protein, the entire protein or, preferably, an antigenic extracellular domain, can be used.

In some embodiments, the sequence of the antigen will be determined from a database, e.g., GenBank, and cloned from a suitable source. In some embodiments, the sequence of the antigen will be determined by sequencing a gene or mRNA (cDNA) of a subject, and cloned from the subject's genetic material, e.g., from nucleic acids taken from the subject. In this way, any genetic variation that might contribute to the antigenicity of the autoantigen can be taken into account.

Multimerization Domains

The multimeric antigens used in the methods described herein include a multimerization domain. In some embodiments, this domain is expressed as part of the multimeric antigen, e.g., as a fusion protein. A preferred multimerization domain is streptavidin, which has the advantage of being amenable to in vitro translation methods for production of protein, and the automatic formation of tetramers during the in vitro translation process. Other multimerization domains include a reactive cysteine (Cys) tag, which can be used to attach the antigens to an appropriate macromolecule, such as a high molecular weight dextran, microspheres or beads, that will bind Cys or can be derivatized to bind Cys; or multimerizing domains from other proteins such as IgG, IgM, or viral capsid proteins that spontaneously self-assemble into spheres to create highly multimeric forms, such as the Hepatitis B core protein (see, e.g., Pumpens and Grens, FEBS Letters. 444:126 (1999)). Alternatively, the antigens can be multimerized by biotinylation and reaction with streptavidin or neutravidin (see, e.g., Newman et al., J. Imm. Methods 272:177-187 (2003)), or by attachment to dextran particles or beads, e.g., collectible beads such as magnetic beads. Although dimerized antigens may be used, higher order multimers are preferred, e.g., trimers, tetramers, or more.

Construction of the multimerized antigens can be achieved using methods known in the art, e.g., standard molecular biological techniques. See, e.g., Sambrook et al., *Molecular Cloning: A Laboratory Manual,* 3rd ed., (2001) Cold Spring Harbor Laboratory, Cold Spring Harbor Laboratory Press, Cold Spring Harbor, N.Y.; Harlow and Lane, *Antibodies: A*

*Laboratory Manual*, (1988) Cold Spring Harbor Laboratory Press, Cold Spring Harbor, N.Y.

Linkers

In some embodiments, the auto-antigen domain will be linked to the multimerization domain via a flexible linker. The linker will typically be from about 4 to 12 amino acids in length, and will include amino acids that do not constrain the structure of the multimer, e.g., alanine and guanine. In some embodiments, the sequence will be GSGMGMGMGMM (SEQ ID NO:7).

Labels

In some embodiments, the multimeric antigens will be labeled. The term "labeled" is intended to encompass direct labeling by coupling (i.e., physically linking) a detectable substance to the multimeric antigen, as well as indirect labeling of the multimeric antigen by reactivity with a detectable substance. Examples of detectable substances include various enzymes, prosthetic groups, fluorescent materials, luminescent materials, bioluminescent materials, and radioactive materials. Examples of suitable enzymes include horseradish peroxidase (HRP), alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, and quantum dots, dichlorotriazinylamine fluorescein, dansyl chloride or phycoerythrin; an example of a luminescent material includes luminol; examples of bioluminescent materials include green fluorescent protein and variants thereof, luciferase, luciferin, and aequorin, and examples of suitable radioactive material include $^{125}I$, $^{131}I$, $^{35}S$ or $^{3}H$. Methods for producing such labeled multimeric antigens are known in the art.

Nucleic Acids and Host Cells

Also encompassed within the present invention are nucleic acids that encode the multimeric antigens, e.g., the MOG, CD2, or MBP antigens. Such nucleic acids can be constructed using methods known in the art, and can be included in an expression vector, e.g., a vector suitable for use in in vitro translation, or a viral or other vector suitable for use in production of recombinant multimeric antigen protein. A number of such vectors are known in the art, and the choice of a vector will depend on the expression method selected. The design of the expression vector can depend on such factors as the choice of the host cell to be transformed, the level of expression of protein desired, and the like.

Typically, the expression vectors include one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. See, e.g., Sambrook et al., *Molecular Cloning: A Laboratory Manual,* 3rd ed., (2001) Cold Spring Harbor Laboratory, Cold Spring Harbor Laboratory Press, Cold Spring Harbor, N.Y.

The expression vectors described herein can be introduced into host cells using methods known in the art, to thereby produce recombinant multimeric antigens, encoded by nucleic acids as described herein. For example, the cells can be transfected using the calcium phosphate or calcium chloride co-precipitation methods, DEAE-dextran-mediated transfection, lipofection, or electroporation. Other suitable methods for transfecting host cells can be found in Sambrook et al., *Molecular Cloning: A Laboratory Manual.* 2nd, ed., Cold Spring Harbor Laboratory, (1989) Cold Spring Harbor Laboratory Press, Cold Spring Harbor, N.Y.

A number of suitable host cells are known in the art; in some embodiments, where post-translational modifications are known or suspected to affect the antigenicity of the autoantigen, a mammalian, e.g., human, host cell line can be used. Glycosylation can also be used in some circumstances to affect the specificity of the multimeric antigen, as there are differences in glycosylation of the major myelin proteins between the central nervous system, where they are not glycosylated, and the peripheral nervous system, where they are glycosylated. Suitable host cells are discussed further in Goeddel, (1990) *Gene Expression Technology: Methods in Enzymology* 185 (Academic Press, San Diego, Calif.).

Methods of Diagnosis Using Multimeric Antigens

The multimeric antigens and methods using the same as described herein offer a number of advantages over previously described techniques for autoantibody detection. Multimerization of the antigen substantially increases the sensitivity of detection, enabling identification of antibodies that have a low binding affinity or are present at low concentrations. In vitro translation with ER microsomes enables rapid expression of radiolabeled proteins that require disulfide bond formation, glycosylation, and chaperone-assisted folding. These fusion proteins spontaneously form SDS-stable multimers in the presence of biotin. The assembled streptavidin (SA) tetramer is resistant to a variety of denaturing agents, permitting selective unfolding of the antigen domain for assessment of conformation-sensitive antibody binding. The assay can be multiplexed by combining multiple radiolabeled tetramers that differ in molecular weight, such as the MOG-SA and CD2-SA tetramers described here.

Tetrameric radioimmunoassay (T-RIA) offers a high level of specificity, as no antibodies were detected in control sera. In contrast, antibodies to denatured MOG or MOG peptides have been reported using Western blotting or ELISA techniques in healthy subjects and patients with non-CNS autoimmune conditions (Reindl et al., Brain, 1999, 122 (Pt 11):2047-56). Berger and colleagues claimed that IgM antibodies to MOG as measured by Western blotting represent a marker for prediction of clinically definite MS (Berger et al., N. Engl. J. Med., 2003, 349(2):139-45), but the lack of a control protein makes it impossible to assess whether the observed binding was indeed MOG-specific. In general, radiolabeled antigens provide a more quantitative and objective readout than ELISA and Western blot assays with enzymatic substrates. Radioimmunoassays for islet antigens have an excellent track record for early detection of type 1 diabetes (Yu et al., Proc. Natl. Acad. Sci. U.S.A., 2000; 97(4):1701-6; LaGasse et al., Diabetes Care, 2002, 25(3):505-11; Barker et al., J Clin Endocrinol Metab 2004, 89(8):3896-902), but due to the monomeric nature of the antigen such assays are optimized for the detection of autoantibodies of relatively high affinity. The tetramer-based approach described here permits detection of autoantibodies to membrane proteins that are difficult to detect with classical radioimmunoassay techniques, and enables incorporation of multiple controls to assess specificity.

Extensive studies in EAE models have demonstrated that only antibodies that recognize folded MOG protein are pathogenic, while antibodies that bind solely to denatured protein or short synthetic peptides fail to induce demyelination (von Budingen et al., Eur J Immunol 2004, 34(8):2072-83; Brehm et al., J Neuroimmunol 1999, 97(1-2):9-15). Also, the co-crystal structure of MOG and the pathogenic murine 8-18C5 antibody revealed that the antibody binds to a surface created by three discontinuous loops and the N-terminus (Breithaupt et al., Proc. Natl. Acad. Sci. U.S.A., 2003, 100(16):9446-51). Commonly used techniques permit detection only of autoantibodies directed against linear epitopes on denatured proteins (Western blot) or do not adequately discriminate between denatured and folded proteins (ELISA), and are thus not optimized for the detection of conformation-dependent autoantibodies (Berger et al., N. Engl. J. Med., 2003, 349(2): 139-45; Mathey et al., Eur J Immunol 2004, 34(8):2065-71).

The results described herein identified MOG autoantibodies that bind to folded MOG protein in a subgroup of ADEM patients, and extensive studies in the EAE model have demonstrated that MOG autoantibodies can induce demyelination (Linington et al., Am J Pathol 1988, 130(3):443-54; Schluesener et al., J Immunol 1987, 139(12):4016-21; von Budingen et al., Eur J Immunol 2004, 34(8):2072-83; Brehm et al., J Neuroimmunol 1999, 97(1-2):9-15). Because only small quantities of serum are currently available from these patients, it has not yet been possible to directly test their pathogenicity by passive transfer experiments in EAE models. ADEM is heterogeneous in terms of clinical presentation and responsiveness to particular treatment approaches (Wingerchuk et al., Curr Neurol Neurosci Rep 2003, 3(3): 256-64; Dale et al., Brain 2000, 123 Pt 12:2407-22; Tenembaum et al., Neurology 2002, 59(8):1224-31; Idrissova et al., Eur. J. Neurol., 2003, 10(5):537-46; Marchioni et al., Neurology 2005, 65(7):1057-65), and the data described herein suggest that this heterogeneity is at least in part due to different mechanisms of pathogenesis.

The response of certain ADEM patients to plasmapheresis or intravenous immunoglobulins suggests that pathogenic autoantibodies play an important role in certain patients (Kanter et al., Neurology 1995, 45(4):824-7; Khurana et al., Pediatrics 2005, 116(2):431-6). It is already well established that plasmapheresis improves outcome in patients with Guillain-Barré syndrome (French Cooperative Group on Plasma Exchange in Guillain-Barré Syndrome, Ann. Neurol. 1987, 22(6):753-61), an antibody-mediated demyelinating disease of the peripheral nervous system. The methods described herein can be used to prospectively determine whether patients with autoantibodies, e.g., MOG autoantibodies, benefit from plasmapheresis or other approaches that target autoantibodies or B cells/plasma cells, by measuring differences in plasma levels of the autoantibodies before and after the treatment.

Moreover, the identification of MOG autoantibodies in a subset of ADEM patients can provide important prognostic information, as described herein; see, e.g., Example 6.

Methods of Diagnosis Using Protein Arrays

Described herein are a number of methods for diagnosing autoimmune diseases by detecting the presence of certain autoantigens. The methods can include, but are not limited to, using immobilized antigens, e.g., antigens on protein arrays, multimeric antigens, or both, e.g., array profiling of autoantibodies targeting both native and linear epitopes.

As described herein, protein arrays are useful for diagnosing ADEM, and in particular for providing a diagnosis of ADEM and ruling out MS. Protein arrays useful in these methods include both native and linear epitopes from MOG, MOBP and MBP. The MBP epitope can include all of, or sequences derived from (i.e., part of), myelin basic protein isoform 1, GenBank Acc. No. NP_001020252.1. The MOBP epitope can include all of, or sequences derived from, GenBank Acc. No. BAA05660.1. The MOG epitope can include all of or sequences derived from GenBank Acc. No. AAH35938.1. Epitopes for use in the arrays can be selected using any method known in the art. For example, the array can include overlapping peptides derived from the full sequence, e.g., peptide scanning. See, e.g., Epitope Mapping: A Practical Approach, Westwood and Hay, Eds. (Oxford Univ. Press 2001), and Robinson et al., Nat. Biotechnol., 2003, 1(9): 1033-9. The array can also or alternatively include epitopes selected using computational methods that predict antigenicity. See, e.g., Kulkarni-Kale et al., Nucl. Acids Res., 2005, 33:W168-W171; Kolaskar and Tongaonkar, FEBS Lett. 1990, 276(1-2):172-4.

For example, the arrays can include at least four, five, six, seven, eight, nine, ten, eleven, or all twelve of the antigenic protein fragments listed in Table 4, e.g., hMBP 80-102, rMBP 10-20, MBP 9-20 Ac, hMOBP 51-70, MBP 85-99, rMOG 7-24, MOG P15, rMOG 25-42, mMOG 79-96, hMBP 20-28, hMBP 29-37, and hMBP 1-20.

Methods for making and using such arrays are well known in the art, see, e.g., Robinson et al., Nat. Biotechnol., 2003, 21(9):1033-9.

Serum obtained from a subject suspected of having an autoimmune disease, e.g., ADEM or MS, is contacted with such an array, and the presence of autoantibodies that recognize these antigens is evaluated, e.g., using methods known in the art or described herein. The presence of autoantibodies that bind to some or all of these antigens (the more that are present, the greater the confidence in the result) indicates an increased likelihood that the subject has ADEM, and should be treated accordingly.

Although arrays are a convenient method of detecting the presence of multiple autoantibodies in a sample, other methods known in the art can be used, e.g., using parallel or serial detection methods. For example, to detect all twelve of the autoantigens listed in Table 4, twelve reactions can be performed, e.g., simultaneously or serially. Alternatively, the reactions can be pooled, e.g., two or more can be performed together, so long as the formation of specific antibody/antigen complexes for each antigen can be detected. Methods for doing so are known in the art.

Multiple Sclerosis (MS)

MS is typically characterized clinically by recurrent or chronically progressive neurologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease. A potential diagnosis of MS may be made using the McDonald criteria, or the revised McDonald criteria (Polman et al., Ann. Neurol., 2005, 58:840-846). For example, a diagnosis of MS can be based on clinical and magnetic resonance imaging (MRI) criteria that document the occurrence of at least two CNS white matter lesions separated in space and time (McDonald et al., Ann. Neurol., 2001, 50(1):121-7).

MOG has been extensively studied as a potential target antigen for autoantibodies in MS (Gaertner et al., Neurology, 2004, 63(12):2381-3; Berger et al., New Engl. J. Med., 2003, 349(2):139-45; Lampasona et al., Neurology, 2004, 62(11): 2092-4; Lim et al., Multiple Sclerosis 2005, 11(4):492-4; Lindert et al., Brain, 1999, 122(Pt 11):2089-100; Reindl et al., Brain, 1999, 122(Pt 11):2047-56), but the presence and involvement of such autoantibodies is controversial. Berger and colleagues claimed that IgM antibodies to MOG represent a marker that enables prediction of clinically definite MS in patients with a clinically isolated syndrome (Berger et al., New Engl. J. Med., 2003, 349(2):139-45), but other studies have failed to confirm these findings (Lampasona et al., Neurology, 2004, 62(11):2092-4; Lim et al., Multiple Sclerosis, 2005, 11(4):492-4). Although oligoclonal IgG is often found in the cerebrospinal fluid (CSF) of MS patients, the specificities of these locally produced antibodies and their role in disease progression are not known. A substantial fraction of patients with neuromyelitis optica, a variant of MS in which optic nerves and the spinal cord are primarily affected, were recently shown to have autoantibodies against the aquaporin-4 water channel that is localized to the astrocytic foot processes at the blood brain barrier, demonstrating that a particular form of demyelinating disease can be associated with autoantibodies against a defined structure (Lennon et al., J. Exp. Med., 2005, 202(4):473-7).

Autoantibodies to MOG and MBP have been detected on myelin sheaths in active MS lesions using gold-labeled synthetic peptides (Genain et al., Nat. Med., 1999, 5(2): 170-5), and autoantibodies to MBP and MOG have been isolated by affinity chromatography from CNS tissue of MS patients (O'Connor et al., J. Immunol., 2005, 175(3):1974-82; Warren et al., Proc. Natl. Acad. Sci. U.S.A., 1995, 92(24):11061-5). A recent study utilized a cell based assay to examine serum samples from MS patients for the presence of MOG autoantibodies (Lalive et al., Proc. Natl. Acad. Sci. U.S.A., 2006). CHO transfectants that expressed MOG were compared to non-transfected cells following incubation with serum samples by FACS and results were expressed as the binding ratio between transfected and non-transfected cells. Low-level staining for MOG was observed with a small fraction of MS serum samples even though high serum concentrations (1:10 dilution, corresponding to ~1 mg/ml of IgG) were used (binding ratio between 1.25 and 1.75 for 2 of 36 samples from patients with a clinically isolated syndrome and 1 of 35 samples from relapsing-remitting MS patients). No Ig family control protein was used, an aspect that is important given the number of Ig family proteins. Both B cells and plasma cells show evidence of an antigen-driven response within MS lesions, and it is possible that autoantibody production in MS is highly localized to the CNS parenchyma and that a low level of autoantibody synthesis makes detection in CSF or serum difficult. Deposition of IgG and complement components on myelin have been demonstrated in MS lesions (Lucchinetti et al., Ann. Neurol., 2000, 47(6):707-17), but it is not known whether MOG or MBP are major targets for such autoantibodies or whether the key target antigen(s) for autoantibodies in MS remain to be identified.

Despite the sensitivity of the methods described herein, autoantibodies to folded MOG protein could not be detected in the serum or CSF of the majority of MS patients. Furthermore, autoantibodies to linear MOG, MBP, or MOBP protein could not be detected in the majority of MS patients, or in patients with viral encephalitis. The data described herein demonstrate that MOG is a more prominent target autoantigen in a subgroup of ADEM patients than in patients with adult-onset MS; in fact, the data described herein indicate that MS is not associated with the presence of conformational autoantibodies to MOG in serum or CSF, and is not associated with the presence of linear or conformational autoantibodies to MOBP, MBP, or MOG. Thus, the methods described herein can be used to rule out a diagnosis of MS.

ADEM

Acute disseminated encephalomyelitis (ADEM) is a widespread demyelinating condition that principally affects the brain and spinal cord, and typically occurs following an infection or vaccination.

Unlike MS, ADEM typically has a rapidly progressive clinical presentation that often includes encephalopathy, reflecting the multi-focal nature of this clinical entity (Wingerchuk et al., Curr. Neurol. Neurosci. Rep., 2003, 3(3):256-64). The disease course is usually self-limiting, although in a minority of cases relapses may occur (multi-phasic demyelinating encephalomyelitis, MDEM) (Dale et al., Brain, 2000, 123 Pt 12:2407-22; Tenembaum et al., Neurology, 2002, 59(8):1224-31). In some cases, clinically definite MS appears to develop following an initial ADEM event (Mikaeloff et al., J. Pediatr., 2004, 144(2):246-52), however the pathogenic relationship between MS and ADEM is unclear, and it remains to be determined if ADEM and MS are related in the spectrum of demyelinating diseases, or if they are entirely separate disease entities.

It is important to distinguish post-vaccinial forms of ADEM, which are the direct result of an immunological response to vaccines contaminated with myelin proteins, from the majority of ADEM cases, which follow an infectious disease, most commonly viral infections. In some cases, no clear antecedent history of either is present. Cell culture-based rabies vaccines are now available, but early-generation vaccines were prepared from rabies-infected CNS tissue and contaminated with MBP (~28 µg/ml) (Javier et al., J. Neurol. Sci., 1989, 93(2-3):221-30). Approximately 1 of 400 vaccine recipients developed major neurological complications, the occurrence of which strongly correlated with the presence of serum autoantibodies to MBP (Hemachudha et al., N. Engl. J. Med., 1987, 316(7):369-74). Similarly, some recipients of a Japanese encephalitis vaccine prepared from infected neonatal mouse brains developed neurological complications (Plesner et al., Eur. J. Neurol., 1998, 5(5):479-85).

The evidence for an autoimmune process is less conclusive for post-infectious forms of ADEM than the evidence provided in these vaccine-related cases. While a modest proliferative T cell response to MBP has been observed in some patients with post-infectious forms of ADEM (Johnson et al., N. Engl. J. Med., 1984, 310(3):137-41; Lisak et al., Neurology, 1974, 24(6):560-4; Pohl-Koppe et al., J. Neuroimmunol., 1998, 91(1-2): 19-27), the diagnosis is still primarily based on exclusion of CNS infection or other causes of acute demyelination. Post-infectious forms of ADEM typically begin within 2-21 days after an infectious event, and have been commonly associated with rubella, varicella, (Idrissova et al., Eur. J. Neurol., 2003, 10(5):537-46) influenza and enteroviral infections, however a variety of other viral and bacterial triggers have also been described (Menge et al., Arch. Neurol., 2005, 62(11):1673-80; Murthy et al., Pediatrics, 2002, 110(2 Pt 1):e21).

The clinical presentation of post-infectious forms of ADEM is often very similar to the presentation of viral encephalitis, which poses significant diagnostic and management difficulties, since very different treatment approaches are required.

Additional information regarding ADEM and MS is available in the art, see, e.g., Rust, Semin. Pediatr. Neurol., 7(2): 66-90 (2000); Brass et al., Pediatr. Neurol., 29(3):227-31 (2003); Menge et al., Arch. Neurol., 62(11):1673-80 (2005).

As described herein, subjects with ADEM, in contrast to subjects with viral encephalitis or MS, have detectable levels of autoantibodies to MOG, MOBP, and MBP. In addition, subjects with ADEM, in contrast to subjects with viral encephalitis or MS, have detectable levels of autoantibodies to folded MOG. Thus, the presence of these autoantibodies in the CSF and/or serum can be used to diagnose a subject with ADEM.

Methods of Treatment

In subjects in which the presence of autoantibodies, e.g., low-affinity autoantibodies, has been confirmed, a treatment can be selected. For example, the presence of autoantibodies indicating the presence of ADEM suggests the selection of a treatment for ADEM, e.g., treatment that suppresses the immune response. For example, conventional treatments for ADEM, including intravenous corticosteroids such as methylprednisone, or adrenocorticotrophic hormone, can be administered. Alternatively or in addition, intravenous immunoglobulin can be administered. Plasmapheresis has also been shown to be effective in certain cases. See, e.g., Kanter et al., Neurology 45(4):824-7 (1995); Khurana et al., Pediatrics 116(2):431-6 (2005); and Garg, Postgrad. Med. J. 79:11-17 (2003).

As one example, the tetrameric antigens described herein can also be used in immunoadsorption plasmapheresis treatments. General methods for immunoadsorption plasmapheresis are known in the art, see, e.g., Amagai et al., J Invest Dermatol. 104(6):895-901 (1995); Hashimoto et al., J. Rheumatol. 18(4):545-51 (1991); Kadar and Borberg, Transfus Sci. 11(2):223-39 (1990); Arakawa et al., Brain Dev. 27(6):431-3 (2005). Epub 2004 Dec. 8; and Takei et al., J. Nippon Med. Sch. 69(6):557-63 (2002). In some embodiments, blood is removed from a subject and plasma is separated from the cellular component, e.g., using a membrane-type plasma separator. The plasma is then contacted with the tetrameric antigen, e.g., immobilized on a column or on a collectible substrate such as beads, e.g., magnetic beads, that allow the substantial removal of autoantibodies from the plasma. The autoantibodies are removed, and the cleaned plasma is then returned to the subject. These methods can be performed once or multiple times, e.g., every day or every other day, e.g., for a number of days.

Methods of Evaluating a Treatment

The tetrameric antigens described herein can also be used to monitor the effectiveness of a treatment, e.g., by measuring the level of autoantibodies in the subject's CSF or plasma. For example, a baseline level of autoantibodies can be established before the treatment is initiated. The baseline level can be established using a level of autoantibodies that was determined for diagnostic purposes, or a level obtained at a later time point. A treatment is then administered, e.g., one or more doses of a treatment, and the level of autoantibodies is determined again. A decrease in the level of autoantibodies will generally indicate that the treatment is effective, while no change or an increase will generally indicate that the treatment is ineffective or harmful. Quantitative and semi-quantitative methods for determining the amount of autoantibodies per volume of blood are known in the art.

EXAMPLES

The invention is further described in the following examples, which do not limit the scope of the invention described in the claims.

Example 1

Tetrameric Antigens for Radioimmunoassay (RIA)

Solution-phase binding of antibodies to radiolabeled autoantigens has proven to be a powerful technique for identification of pre-diabetic individuals (Yu et al., Proc. Natl. Acad. Sci. U.S.A., 2000, 97(4):1701-6; LaGasse et al., Diabetes Care, 2002, 25(3):505-11; Barker et al., J. Clin. Endocrinol. Metab., 2004, 89(8):3896-902), but monovalent binding only enables the detection of autoantibodies with relatively high affinities for their target antigen. In animal models of antibody-mediated autoimmunity, such as hemolytic anemia, low affinity autoantibodies can be highly pathogenic in vivo if they are directed against membrane proteins, because antigen clustering enables bivalent antibody binding (Fossati-Jimack et al., J. Exp. Med., 1999, 190 (11):1689-96). Multimeric ligands have proven useful for detection of antigen-specific T and B cells (Newman et al., J. Immunol. Methods, 2003, 272(1-2):177-87 (biotinylated fluorochrome labeled tetramers); Altman et al., Science, 1996, 274(5284):94-6 (biotinylated peptide-MHC multimers). The experiments described herein in part investigated whether increasing the valency of a target antigen would permit detection of rare and/or low affinity antibodies, by enabling bivalent binding.

Figure 1B:
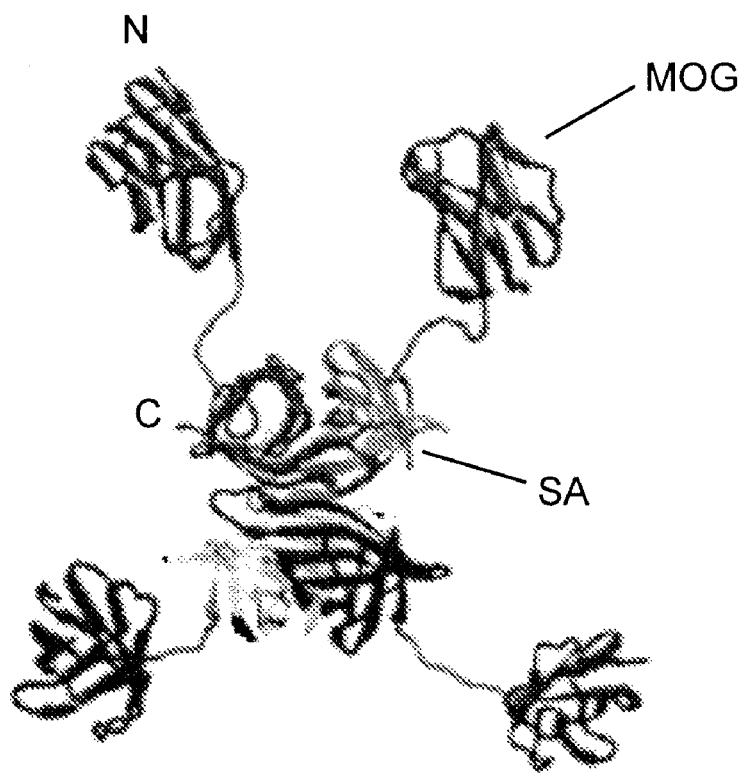
FIG. 1B is a model of the crystal structures of MOG and SA (PDB numbers PY9 and 1 SW) were used to model the MOG-SA structure (the four MOG domains are exposed on the outside of the molecule, while the four SA domains are clustered in the center). The N- and C-termini of the SA monomer are solvent exposed on the same face, which enabled attachment of the antigen at either site.

As described herein, a series of multimeric antigens was designed based on the ability of the streptavidin (SA) monomer to spontaneously assemble into a tetrameric structure. The extracellular domain of human MOG and a control member of the immunoglobulin superfamily (human CD2) were each connected to a monomer of SA via a flexible linker. In the assembled streptavidin tetramer, the N- and C-termini are within close proximity and solvent-exposed, permitting fusion of the antigen at either terminus. The difference in the molecular weight of MOG and CD2 tetramers enabled inclusion of CD2-SA as an internal control in immunoprecipitation (IP) experiments. FIG. 1A shows a schematic illustration of the MOG-SA and SA-MOG constructs; FIG. 1B is a theoretical model of the constructs.

Expression constructs were generated by PCR using the extracellular domains of human MOG or CD2 joined by a flexible 11 amino acid linker (GSGMGMGMGMM (SEQ ID NO:7) that included glycine for flexibility, and methionine for ease of labeling, e.g., using $^{S}35$) to the 127 amino acid core domain of streptavidin (SA). The murine H-2K$^b$ signal sequence was used for ER targeting. Antigen-streptavidin DNA constructs were ligated into a modified pSP64 vector (provided by M. Kozak) for generation of RNA transcripts using the RiboMax T7 large-scale RNA production kit (Promega, Madison, Wis., USA).

MOG-Streptavidin Fusion Protein

The MOG-SA fusion protein, in which the extracellular domain of human MOG is N-terminal and SA is C-terminal, was produced using the following strategy:

1. Amplified MOG fragment from plasmid C100 using oligos MOG-SA.1 (5' TGTTGGCGGC CGCCCTGGCT CCGACTCAGA CCCGCGCGCA GTTCAGAGTG ATAGGACCAA 3'; SEQ ID NO:9) and MOG-SA.2 (5' GGTGATGCCC GCTTCCGCCA TCATGCCCAT GCCCATGCCC ATGCCGGATC CCCAGTAGAA AGGATCTTCT AC 3'; SEQ ID NO:10).

2. Amplified streptavidin fragment from core streptavidin vector using oligos MOG-SA.3 (5' ATGGCGGAAG CGGGCATCAC C 3'; SEQ ID NO:11) and MOG-SA.4 (5' AAAAAAAAGC TTTTTTTTTT TTTTTTTTTT TTTCAGCTCG CCGCGCTCGG TTTCA 3'; SEQ ID NO:12).

3. Gel purified products and performed overlapping PCR using oligos Leader-HindIII (5' AAAAAAAAGC TTGCCGCCAC CATGGTACCG TGCACGCTGC TCCTGCTGTT GGCGGCCGCC CTGGCT 3'; SEQ ID NO:13) and MOG-SA.4.

4. Digested products with HindIII and cloned them into pSP64 Kozak (Pharmacia Biotech Inc.) that had been digested with HindIII and dephosphorylated.

5. Determined the correct orientation of the insert by performing PCR with Kozak forward and MOG-SA.4.

6. Sequenced with Kozak forward and reverse primers as well as MOG-SA.3.

The sequence of the resulting construct is shown in FIG. 5.

Streptavidin-MOG Fusion Protein

The SA-MOG fusion protein, in which SA is N-terminal and the extracellular domain of human MOG is C-terminal, was produced using the following strategy:

Cloning Strategy:

1. Amplified SA fragment from a MOG-SA clone made as described herein using oligos SA-MOG-swapped.1 (5' TGT-TGGCGGC CGCCCTGGCT CCGACTCAGA CCCGCGCGGC GGAAGCGGGC ATCACCGGCA 3'; SEQ ID NO:14) and SA-MOG-swapped.2.

2. Amplified MOG fragment from MOG-SA clone 2.7 midiprep using oligos SA-MOG-swapped.3 and SA-MOG-swapped.4.

3. Gel purified the products and performed overlapping PCR using oligos Leader-HindIII and SA-MOG-swapped.4.

4. Digested with HindIII and cloned into pSP64 Kozak that had been digested with HindIII and dephosphorylated.

5. Determined the correct orientation of the insert by PCR with Kozak forward and SA-MOG-swapped.4.

6. Sequenced with Kozak forward and reverse primers as well as SA-MOG-swapped.3.

The sequence of the resulting construct is shown in FIG. 6.

MOG Monomer Protein

The MOG monomer protein, including the extracellular domain of human MOG and a linker, was produced using the following strategy:

1. Amplified MOG and linker from MOG-SA vector produced as described herein using oligos Leader-HindIII and MOG-mono-rev (5' AAAAAAAGCT TTTTTTTTTT TTTTTTTTTT TTCACATCAT GCCCATGCCC ATGCC 3'; SEQ ID NO:16)

2. Gel purified the product, and digested with HindIII.

3. Cloned into pSP64 Kozak that had been digested with HindIII and dephosphorylated.

4. Determined the orientation with Kozak forward and MOG-mono-rev primers.

5. Sequenced with Kozak forward and reverse primers.

The sequence of the resulting construct is shown in FIG. 7.

In Vitro Translation

The in vitro translation system has been used to generate $^{35}$S-labeled proteins for detection of autoantibodies to antigens that do not require targeting to the endoplasmic reticulum (ER) for disulfide bond formation and glycosylation. To enable folding of the MOG Ig domain in a native ER environment, an in vitro translation system with ER microsomes isolated from a murine hybridoma cell line was used (Call et al., Cell, 2002, 111(7):967-79). Briefly, in vitro translation was performed using ER microsomes isolated from a murine hybridoma cell line (Call et al., Cell, 2002, 111(7):967-79) in rabbit reticulocyte lysate (Promega) supplemented with $^{35}$S-labeled methionine (final activity 0.3 µCi/µL, Amersham Biosciences, Piscataway, N.J., USA), unlabeled amino acids minus methionine (Promega, final concentration 20 µM each), 2% SUPERaseIn RNAse inhibitor (Ambion, Austin, Tex., USA), 160 µM biotin (Sigma, St. Louis, Mo., USA), and 8 ng/µL RNA. Translation of CD2-SA took place in 250 µL aliquots, each for 10 IP reactions. MOG-SA translation reactions were 180 µL per 10 IPs.

Proteins were translated at 30° C. under reducing conditions for 1 hour, followed by 2 hours under oxidizing conditions (addition of oxidized glutathione (Sigma) to a final concentration of 4 mM) to enable formation of disulfide bonds. The ER membrane fraction was washed with cold stopping buffer (PBS, 10 mM iodoacetamide (Sigma), 160 µM biotin) and proteins were released by addition of NP-40 (Pierce Biotechnology, Rockford, Ill., USA) to 0.5%. Tetramers of CD2 and MOG were combined and filtered (Spin-X 0.2 micron, Corning Incorporated, Corning, N.Y., USA). 5 µL of the combined antigen was stored at 4° C. as a reference, and the remainder was cleared against Protein A—Sepharose™ CL4B (Amersham, 10% final concentration) in 500 µL of RIA buffer (PBS, 1% BSA (Sigma), 0.1% Tween-20, 160 µM biotin) to reduce nonspecific binding.

Cleared antigens were filtered to remove Sepharose™ beads and the volume was increased with RIA buffer. 25 µL of labeled antigen was added to serum diluted in RIA buffer for a final volume of 250 µL. IP reactions with cerebrospinal fluid were carried out using 200 µL of CSF and 50 µL of RIA buffer. Antibody binding took place overnight at 4° C. on an orbital rotator. Immunoglobulins and bound radiolabeled antigens were isolated by incubation with 20 µL of Protein A-Sepharose™ CL4B beads or anti-IgM (Medix Biochemica, Kauniainen, Finland) coupled to Sepharose™ 4 (Amersham) for 90 minutes. Sepharose™ beads were washed twice with 1 mL of RIA buffer, and bound proteins were eluted at 4° C. in 10 µL of 50 mM CAPS, pH 11.5. The supernatant was filtered into 10 µL of LDS gel loading buffer (Invitrogen, Carlsbad, Calif., USA) containing 160 µM biotin, 100 mM sodium phosphate pH 6.0, 100 mM DTT, and protease inhibitors (1 mM EDTA, 2 µg/mL aprotinin, 2 µg/mL leupeptin, 1 g/mL pepstatin A (Roche Applied Science, Indianapolis, Ind., USA)).

When digestion with Endoglycosidase H (New England Biolabs, Ipswich, Mass., USA) was performed, 1000 units of the enzyme were added and samples incubated at 37° C. for 2 hours.

Samples were then loaded onto 4-12% NOVEX Bis-Tris gels and run in MOPS buffer (Invitrogen). Proteins were electro-transferred to a PVDF membrane (Bio-Rad, Hercules, Calif., USA) and dried membranes were exposed to a phosphor imager screen (Molecular Dynamics, Amersham) for quantification of incorporated $^{35}$S-methionine. The amount of tetrameric MOG and CD2 isolated in IP reactions was normalized to the input quantity of each antigen.

Figure 1D:
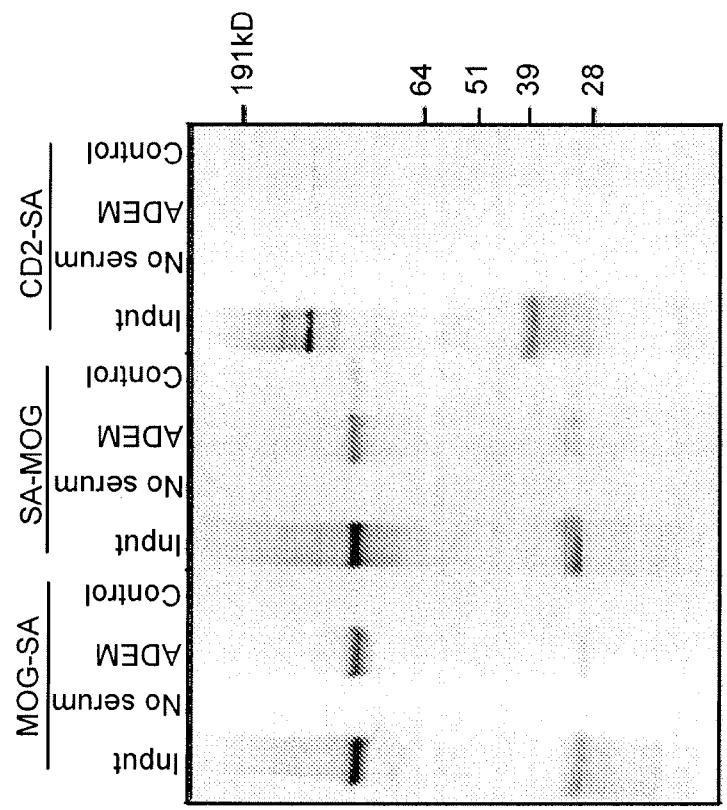
FIG. 1D is an image of a protein gel showing the specific immunoprecipitation (IP) of MOG tetramers by autoantibodies in serum from an ADEM patient (#1724). IP reactions were set up with MOG-SA, SA-MOG and CD2-SA tetramers using no serum, ADEM serum, or a control serum at a dilution of 1:100. Radiolabeled tetramers bound to immunoglobulins were eluted from protein A beads, resolved by SDS-PAGE and transferred to a PVDF membrane for quantification using a phosphor imager. Data were standardized by calculating the percent of radiolabeled tetramer isolated in the IP. Similar quantities of the two MOG tetramers were precipitated by the ADEM sample (45% of MOG-SA and 39% of SA-MOG), while little MOG was immunoprecipitated by the control serum (0.5% of MOG-SA, 2% of SA-MOG). No more than 2% of the CD2 control tetramer was immunoprecipitated in any reaction.
Figure 1C:
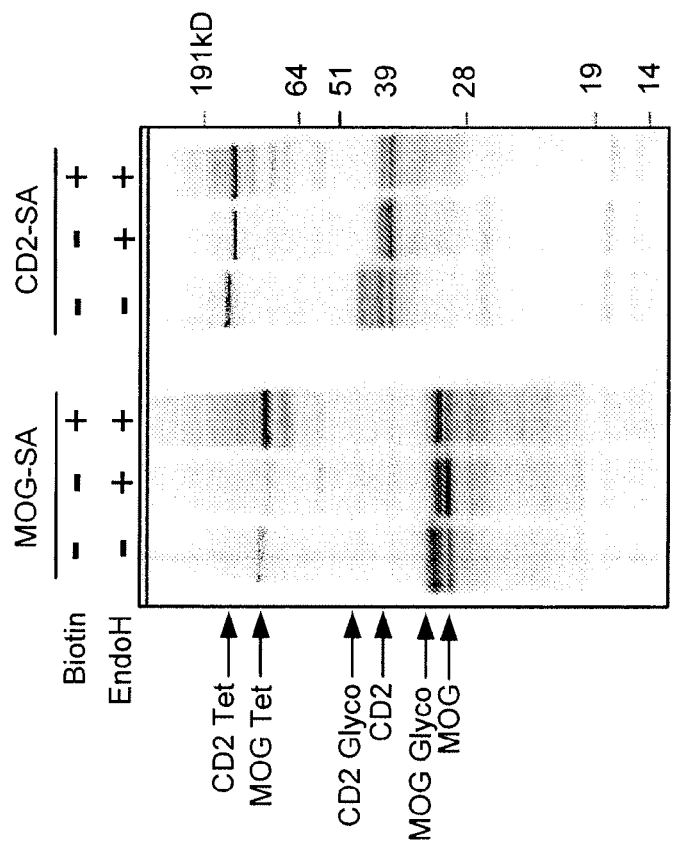
FIG. 1C is an image of a protein gel demonstrating the assembly of MOG-SA and Cluster of Differentiation 2 (CD2)-SA fusion proteins into tetramers. $^{35}$S-labeled proteins were expressed in an in vitro translation system with ER microsomes to enable folding and glycosylation of extracellular Ig domains. Both proteins were glycosylated, indicated by a decrease in molecular weight following digestion with EndoH (lanes 2 and 5). Addition of biotin during translation yielded tetramers stable during SDS-PAGE (lanes 3 and 6).

The signal peptide used for ER targeting was efficiently cleaved and both MOG and CD2 fusion proteins were glycosylated in the ER, as shown by a reduction of molecular weight following digestion with endoglycosidase H (EndoH) (FIG. 1C). Addition of biotin during translation resulted in efficient formation of tetramers that were stable during electrophoresis on SDS gels (FIG. 1C).

Example 2

Confirmation of the Presence of Autoantibodies to MOG in Clinical Samples

To determine if clinical samples contained autoantibodies to MOG, diluted human serum or CSF was incubated overnight with tetrameric antigens made as described in Example 1. The MOG tetramer was immunoprecipitated by serum antibodies from a patient with ADEM (patient 1724), but not by a control serum. The CD2 tetramer was not immunoprecipitated by either sample (FIG. 1D), excluding the possibility that the antibodies were bound non-specifically to either the streptavidin or linker components. Tetramers with an N- or C-terminal position of MOG relative to SA (MOG-SA and SA-MOG, respectively) were equally effective for detection of autoantibodies (FIGS. 1A and 1D).

Example 3

Comparison of Monomeric and Tetrameric Antigens

Figure 2A:
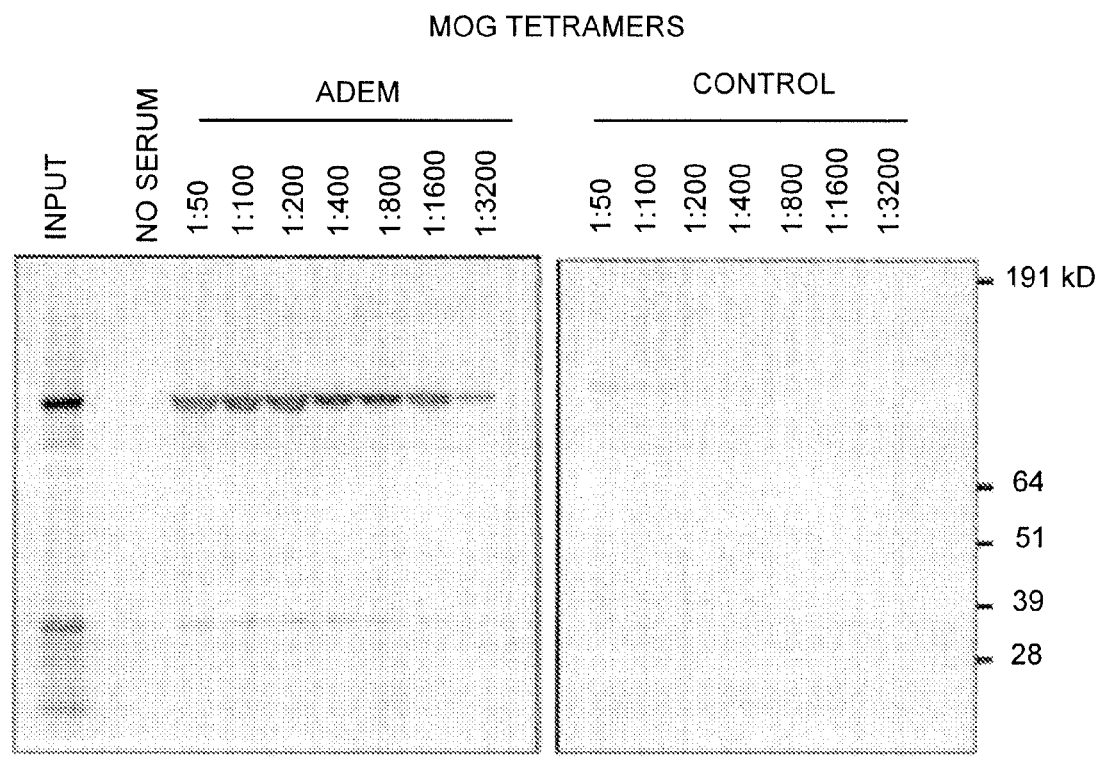
FIGS. 2A-B are images of protein gels of $^{35}$S-labeled MOG-SA tetramers (2A) and MOG monomers (2B) were compared in IP experiments using serial dilutions of ADEM (#1724, left panels) and control sera (right panels). The MOG tetramer provided a stronger signal (19,469 counts at a serum dilution of 1:50) than the MOG monomer (6,920 counts at 1:50 dilution), and enabled detection at higher serum dilutions.
Figure 2B:
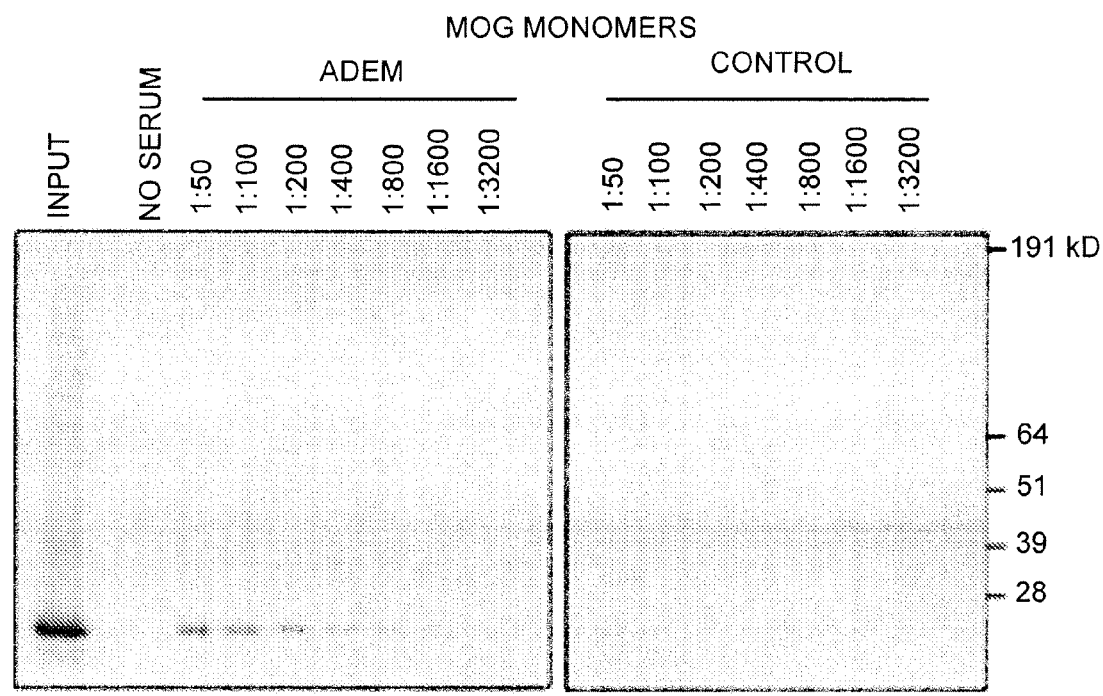
Figure 2C:
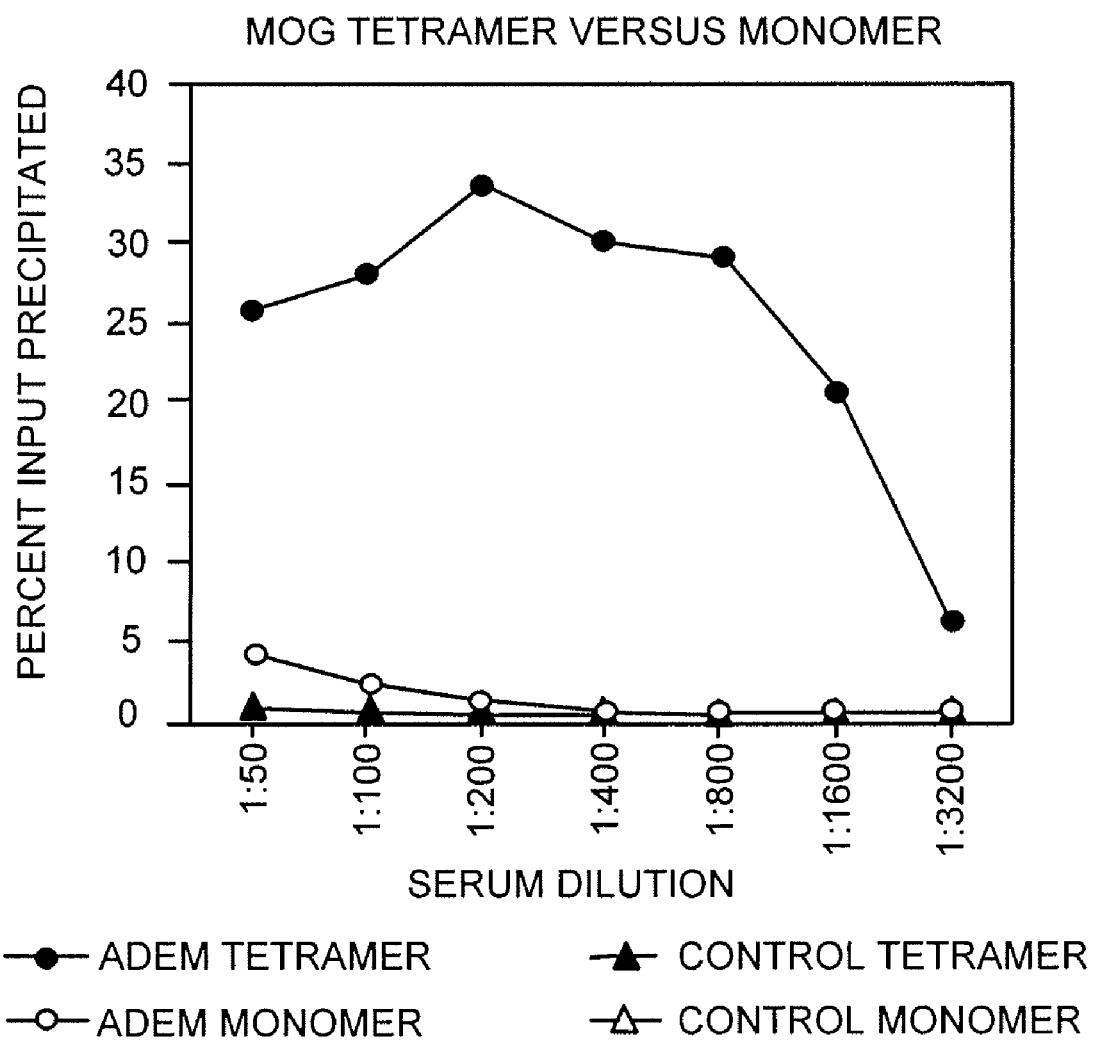
FIG. 2C is a line graph illustrating the results of quantification of data as percentage of input radiolabeled protein. Tetrameric and monomeric versions had the same number of radiolabeled methionine residues per chain.

To determine if this tetramer-based radioimmunoassay was more sensitive than monomer-based detection, monomeric MOG that differed from the tetramer only in the absence of the streptavidin domain was also generated. The module did not contain methionine, which resulted in an identical number of labeled residues. The tetramer greatly increased the sensitivity of autoantibody detection compared to the monomer (FIGS. 2A-C). More than 25% of the MOG tetramer was immunoprecipitated at ADEM serum dilutions of 1:50 to 1:800, compared to less than 5% of the MOG monomer (FIG. 2C). The increase in signal with the tetramer was far greater than the 4-fold greater signal per protein unit, indicating that multivalent binding enabled detection of a larger number of antibody-antigen interactions.

Example 4

Detection of MOG Autoantibodies in Human Demyelinating Disease

This example describes experiments designed to determine whether autoantibodies to conformational determinants of MOG are present in the serum or CSF in different human inflammatory demyelinating diseases. Serum samples were examined from cases of ADEM/MDEM (n=47), different forms of MS (pediatric, n=24; Asian MS, n=12; relapsing-remitting, n=92; primary progressive, n=6; and secondary progressive, n=12) and compared these to control cases of viral encephalitis (n=58) as well as healthy control subjects (n=80).

Cross-sectional patient and control serum samples were collected at the Partners MS Center at the Brigham and Women's Hospital, Boston as well as other international neurological centers that care for adults and/or children with MS and demyelinating diseases. Each site collected samples using a protocol approved by their Institutional Review Board. Serum and CSF samples were stored in aliquots at −80° C.

A detailed clinical intake form was collected from outside investigators, summarizing the patient's neurological history, relapse features, neurological examination, MRI and CSF findings. For samples collected at the Brigham and Women's Hospital, the same information was culled from the MS Center's Oracle-based clinical database. Adult and pediatric patients were diagnosed with relapsing-remitting multiple sclerosis according to the McDonald criteria (McDonald et al., Ann. Neurol., 2001, 50(1):121-7). Pediatric MS was defined as cases of MS with an onset of symptoms prior to 18 years of age. In some cases, pediatric patients were diagnosed with MS after a first event of ADEM and a second non-encephalopathic demyelinating event. ADEM was diagnosed in cases presenting with a polysymptomatic inflammatory demyelinating event, which included encephalopathy. One clinician validated each case included in this study using the data from the clinical intake form. Viral encephalitis serum samples were provided by the New York State Department of Health from patients with serum-positive PCR for enterovirus, West Nile virus or St. Louis encephalitis virus.

Figure 3:
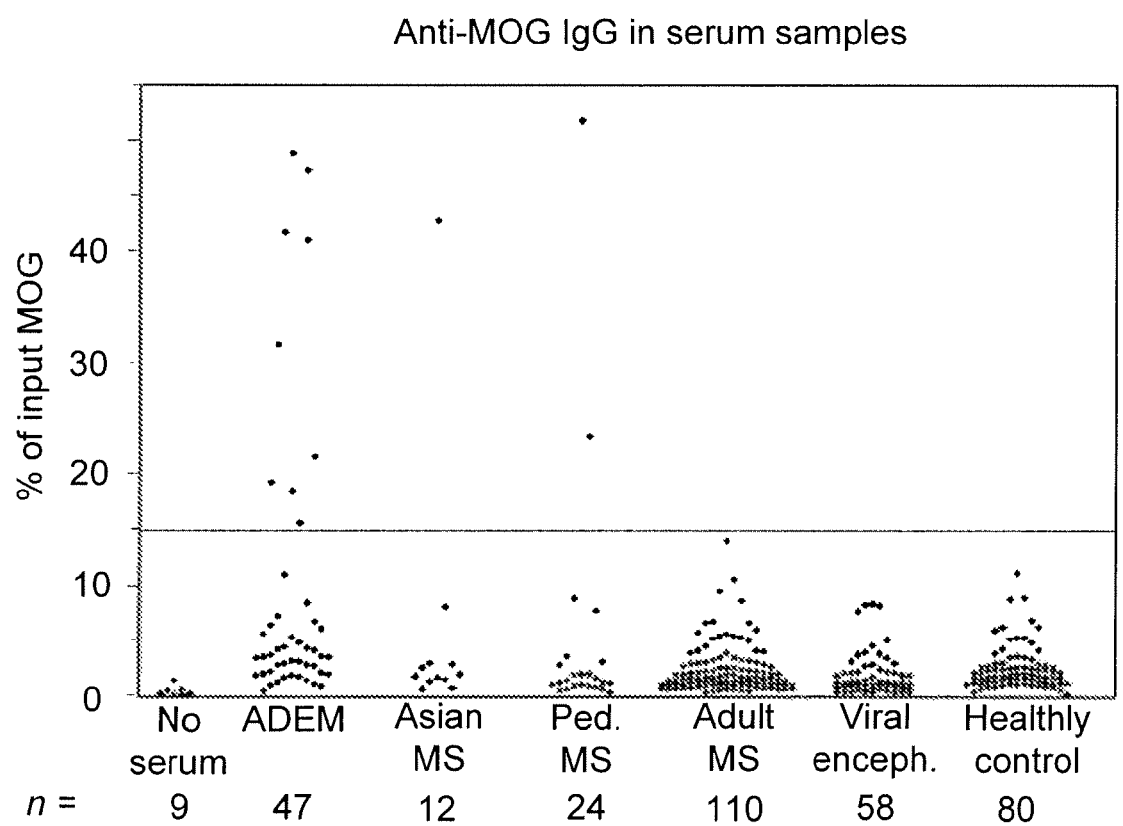
FIG. 3 is a dot plot showing the results of analysis of MOG autoantibodies in CNS diseases. Sera from a subset of patients diagnosed with ADEM (9 of 47 patients, 19%) immunoprecipitated more than 15% of input MOG tetramer. This threshold is 4 standard deviations from the mean for normal controls. MOG autoantibodies were not detected in sera from a large group of patients with encephalitis (n=58), adult-onset MS (n=110) or from control donors (n=80). One Japanese patient and two pediatric patients classified as MS had autoantibodies to MOG; all three of these subjects were non-Caucasian.

Each serum sample was assayed for the presence of antibodies to MOG at a dilution of 1:100. No sample showed binding to the CD2 control tetramer, and no antibodies to MOG were detected in serum samples from healthy donors. All patient samples that precipitated greater than 10% of MOG-SA were repeated in triplicate, and the mean of these measurements was taken. As summarized in Table 2, IgG autoantibodies were identified in the serum of 9 out of 47 ADEM patients, and these sera immunoprecipitated>15% of input MOG tetramer (FIG. 3). Anti-MOG IgM was detected in only one ADEM sample (n=32; insufficient sample volumes precluded analysis of other specimens), which also contained anti-MOG IgG. For 43 of the 47 ADEM samples the precise date of sample collection was available, and the majority of these samples were drawn within 120 days of the initial diagnosis (7 of 9 cases in the MOG$^+$ group, 77.7%, and 25 of 34 cases in the MOG$^-$ group, 73.5%). In one of the MOG$^+$ patients, the sample was obtained 272 days following diagnosis, and in another case 211 days following a relapse (721 days following initial diagnosis).

These data suggest that such autoantibodies can persist for extended periods of time. MOG autoantibodies were absent in patients with viral encephalitis, underscoring the difference between autoimmune processes and viral CNS infections that also cause inflammation.

No serum IgG or IgM autoantibodies to MOG were detected among either 110 subjects with adult-onset MS from North America (Table 1) or the 68 CSF samples from a separate group of subjects with adult-onset MS. One Japanese subject with adult-onset MS, and two subjects with pediatric MS, had detectable anti-MOG IgG. Both of the anti-MOG positive pediatric patients were from minority populations (African American, Pacific Islander of Asian descent). One of these two subjects was initially diagnosed as ADEM but later reclassified as MS following development of bilateral optic neuritis three years after the initial clinical event. The other pediatric patient experienced a relapse eight months after the initial demyelinating event and was diagnosed as MS based on the McDonald criteria (McDonald et al., Ann. Neurol., 2001, 50(1):121-7). No clinical data were available for the Japanese MS patient. All three cases were from ethnic groups known to have a much lower incidence of classical MS than populations of European ancestry.

TABLE 2

Frequency of anti-MOG IgG and IgM in patient sera and CSF

| | Serum Samples | | | | | | CSF Samples | | | |
|---|---|---|---|---|---|---|---|---|---|---|
| | ADEM | Asian MS | Ped MS | Adult MS | Enceph | Control | ADEM | Asian MS | Adult MS | Other |
| IgG | 9/47 | 1/12 | 2/24 | 0/110 | 0/58 | 0/80 | 0/8 | 0/11 | 0/68 | 0/54 |
| IgM | 1/32 | nd | 0/5 | 0/12 | 0/20 | 0/33 | 1/8 | 0/11 | 0/68 | 0/54 |

"Other" CSF samples were from: cadaver (1), cancer (5) ehrlichia (1), ER visit, not MS (10), fever (2), headache (13), head trauma (1) HIV (4), meningitis (4), neurosarcoidosis (1), numbness (1), seizures (2), systemic autoimmune disease (1), and other neurological disease (8).

Example 5

Conformational Sensitivity of MOG Autoantibodies in ADEM

Competition assays were performed to further document the specificity of MOG autoantibody binding. Briefly, monomeric MOG was produced in *E. coli* and refolded (O'Connor et al., J. Immunol., 2005, 175(3):1974-82), and purified aldolase was purchased from Amersham. Indicated amounts of unlabeled protein were incubated with serum in 250 μL of RIA buffer for 3 hours prior to addition of labeled tetrameric antigen, after which reactions were carried out as described above.

Figures 4A, 4B:
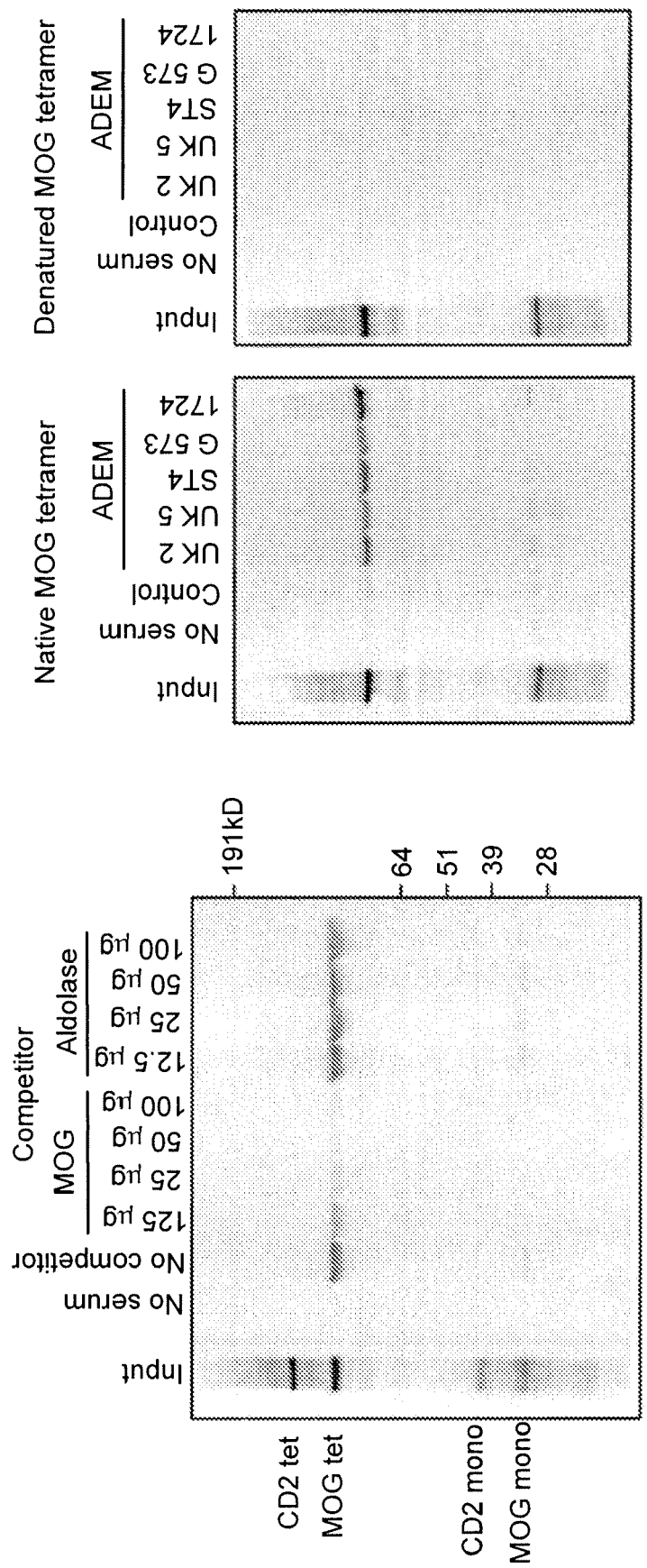
FIG. 4A is an image of a protein gel showing that cold competition of autoantibody binding to MOG tetramers. Serum from an ADEM patient was incubated for 3 hours with the indicated amounts of unlabeled recombinant MOG monomer or control protein (aldolase) prior to addition of radiolabeled MOG tetramer. In the absence of competitor, 37% of MOG-SA and less than 1% of CD2-SA were immunoprecipitated by the ADEM serum. Addition of unlabeled MOG monomer inhibited tetramer binding in a dose-dependent manner (1.1% of MOG tetramer was precipitated in the presence of 50 μg competitor), while aldolase had little effect (29.8% of MOG was precipitated in the presence of 50 μg aldolase).
FIG. 4B is an image of a protein gel showing that autoantibodies identified with the MOG tetramer require the folded MOG structure for binding. The tetrameric structure was maintained but the Ig domain of MOG was unfolded by cleavage of the MOG disulfide bond with DTT (heating to 70° C. for 10 min). All five ADEM sera immunoprecipitated the tetramer with the native MOG structure, but not the tetramer with a denatured MOG Ig domain.

The results of the competition assays further documented the specificity of autoantibody binding. Addition of increasing concentrations of unlabeled folded monomeric MOG expressed in *E. coli* as a competitor dramatically reduced the amount of MOG tetramer precipitated, while an irrelevant protein, aldolase, had little effect (FIG. 4A). The MOG protein used for competition was not glycosylated indicating that the majority of antibodies did not require the glycan for binding.

The tertiary structure of the MOG extracellular domain requires a disulfide bond, so the dependence of antibody binding on the conformation of MOG was also examined.

Denaturation of MOG Ig domain in the tetramers was performed as follows. Tetrameric MOG was produced and released from ER microsomes as above, then divided into two equal portions. To one half, DTT was added to 10 mM and the tetramer was heated at 70° C. for 10 minutes. The other half of the reaction was left on ice. An aliquot of each was taken and stored at 4° C. for reference, and the remainder was cleared as described above. Following removal of the SEPHAROSE™ beads, untreated and denatured antigens were diluted in RIA buffer (250 μL per IP reaction). The final concentration of DTT in the denatured sample was 0.22 mM, and DTT was added to the unheated MOG tetramer to the same final concentration. Sera were added at a dilution of 1:100, and IP reactions were carried out as described above.

Cleavage of this disulfide bond with DTT at 70° C. did not destabilize the tetrameric structure, but the antigen was no longer immunoprecipitated by any of the ADEM sera tested (FIG. 4B). This was not caused by the mildly reducing environment, as DTT was added to the same final concentration to IP reactions with untreated tetramer.

The ability to assay both native and intentionally denatured antigens allows the characterization of low-affinity autoantibodies directed against conformational epitopes that cannot be detected by traditional methods.

Example 6

Clinical Features of ADEM Patients with Anti-MOG Responses

ADEM is a relatively rare entity that occurs predominantly in pediatric patients; therefore sample collections from six different countries were pooled for this study. This sample of 47 cases, while relatively small, is one of the larger collections of ADEM sera and CSF analyzed to date. There does not appear to be a significant preponderance of anti-MOG ADEM cases in any one of the six participating centers. There was no difference in the male/female ratio or the average age between ADEM patients with and without MOG autoantibodies. Although only a subset of patients was tested for CSF oligoclonal bands, there was no correlation between their presence and MOG autoantibodies. ADEM is frequently preceded by infections, but specific pathogenic triggers were not investigated in the cases studied here.

Differences in the clinical presentation between the MOG+ and MOG− groups were observed, as summarized in Table 3. The small number of cases in the MOG+ group (n=9) prevented definitive assessment of statistical significance and these initial findings thus require future analysis of a larger patient population.

TABLE 3

Clinical Presentation Characteristics of the MOG+ and MOG− Groups

|  | Anti-MOG Positive | Anti-MOG negative |
|---|---|---|
| Patient data | | |
| n= | 9 | 38 |
| Percent female | 55.5 | 41.7 |
| Average age at first event | 14 | 8.6 |
| Oldest at first event | 41 | 28 |
| Youngest at first event | 4 | <1 |
| Percent with 2$^{nd}$ event | 22.2 | 16.7 |
| Oligoclonal bands in CSF | | |
| OCB tested for | 4 | 14 |
| OCB present | 1 (25%) | 5 (35.7%) |
| Outcome | | |
| No deficits | 4 (50%) | 24 (70.6%) |
| Residual deficits | 4 (50%) | 10 (29.4%) |
| No improvement | 0 | 0 |
| Death | 0 | 0 |
| Sample Source | | |
| Argentina | 11.1% | 31.6% |
| Germany | 11.1% | 10.5% |
| Japan | 22.2% | 13.2% |
| Canada | 33.3% | 36.8% |
| UK | 22.2% | 5.3% |
| USA | 0 | 2.6% |
| General neurological status | | |
| At least one symptom | 66.6% | 86.1% |
| Focal seizures | 0 | 22.2% |
| General seizures | 11.1% | 13.9% |
| Behavioral changes | 44.4% | 69.4% |
| Lethargy | 55.5% | 72.2% |
| Coma | 11.1% | 13.9% |
| Bilateral and unilateral symptoms | | |
| At least one bilateral symptom | 55.5% | 37.1% |
| At least one unilateral symptom | 11.1% | 54.3% |
| Bilateral motor | 44.4% | 25% |
| Unilateral motor | 11.1% | 41.7% |
| Bilateral sensory | 22.2% | 11.1% |
| Unilateral sensory | 11.1% | 22.2% |
| Bilateral optic neuritis | 11.1% | 11.1% |
| Unilateral optic neuritis | 0 | 16.7% |
| Motor control | | |
| At least one symptom | 33.3% | 61.1% |
| Myoclonus | 0 | 2.3% |
| Tremor | 0 | 16.7% |
| Cerebellar - ataxia | 33.3% | 58.3% |
| Brainstem symptoms | | |
| At least one symptom | 44.4% | 58.3% |
| Facial weakness | 0 | 25% |
| Dysphagia | 11.1% | 19.4% |
| Dysarthria | 22.2% | 22.2% |
| Ophthalmological | 33.3% | 33.3% |
| MRI lesions | | |
| Gadolinium enhancing lesions | 44.4% | 30.6% |
| Single large tumor-like lesions | 11.1% | 5.6% |
| Corpus callosum, other white matter | 44.4% | 41.7% |

TABLE 3-continued

Clinical Presentation Characteristics of the MOG+ and MOG– Groups

|  | Anti-MOG Positive | Anti-MOG negative |
|---|---|---|
| Periventricular white matter | 55.5% | 75.0% |
| Cortical grey matter | 33.3% | 25.0% |
| Subcortical grey matter | 11.1% | 33.3% |
| Lesion location | | |
| Supratentorial | 88.9% | 75.0% |
| Optic nerve | 11.1% | 13.9% |
| Brainstem/cerebellum | 55.5% | 58.3% |
| Spinal | 33.3% | 36.1% |
| MRI burden | | |
| Multifocal | 77.8% | 77.8% |
| Focal | 22.2% | 16.7% |
| MRI feature - T1 black | 11.1% | 19.4% |

In the ADEM cases studied here, patients with MOG autoantibodies had a higher incidence of bilateral motor and sensory symptoms than unilateral symptoms, while the reverse was observed in the MOG⁻ group. Unilateral optic neuritis was absent in the MOG⁺ group, but observed in 6 of 35 (17.1%) autoantibody-negative patients. The greater prevalence of bilateral motor and sensory involvement was not related to an overall more severe clinical presentation because the frequency of behavioral changes, lethargy, coma or generalized seizures was not different between the two groups. In addition, symptoms that can reflect gray matter involvement (myoclonus, tremor and focal seizures) were less prevalent in the MOG⁺ group.

Autoantibodies to MOG were also associated with a less favorable prognosis for recovery: 50% of MOG⁺ patients had residual deficits versus 29.4% of MOG⁻ ADEM patients.

These results demonstrate that the presence of MOG autoantibodies can be used to predict a subjects' prognosis.

Example 7

'Myelin Proteome' Arrays to Profile Autoantibody Response

It was hypothesized that characteristic profiles of autoantibodies exist in MS, and that determination of autoantibody profiles will aid in diagnosis, prognostication, and guiding selection of therapy. Antigen microarray technology was developed to perform multiplex characterization of antibody responses (Robinson et al., Nature Medicine, 8:295-301, (2002)). Antigen arrays contain thousands of proteins and peptides attached to the surface of microscope slides in an ordered array where they can be analyzed for their interactions with antibodies in disease and control samples. "Myelin proteome" arrays contain a spectrum of proteins and peptides derived from the myelin sheath, which are targeted by the autoimmune response in multiple sclerosis (MS) (Robinson et al., Nat. Biotechnol., 2003; 21(9):1033-9).

Myelin Proteome Arrays

Myelin proteome arrays were generated by printing proteins and peptides representing myelin antigens onto poly-L-lysine or epoxy microscope slides using a robotic microarrayer. A 2304-feature myelin proteome array was developed that contained 485 different myelin protein and peptides including myelin basic protein (MBP), proteolipid protein (PLP), myelin oligodendrocyte protein (MOG), golli-MBP, oligodendrocyte-specific protein (OSP), overlapping peptides representing these proteins, as well as peptides representing immunodominant epitopes from additional myelin proteins including cyclic nucleotide phosphodiesterase (CNPase), myelin-associated glycoprotein (MAG), myelin-associated oligodendrocytic basic protein (MBOP), and a variety of bacterial and viral mimics of myelin proteins. Additional antigens were added in an ongoing basis.

125 arrays were produced with each print. Briefly, a microarray printing robot, such as that described by Patrick Brown and colleagues (see, e.g., Robinson et al., Nat. Med., 2002, 8:295-301), deposited 1 pL of solution containing 200 pg of antigen at each feature on the array. Antigen features measured about 200 µm in diameter, and each array contained 4-8 replicate features for each antigen spotted. Arrays were probed with 1:150 dilutions of human serum or 1:10 dilutions of human cerebral spinal fluid (in a total volume of 300 µl) derived from normal humans or humans with ADEM, MS or other neurologic diseases. Following incubation with human sera or CSF, arrays were washed and probed with Cy-3-conjugated donkey-anti-human IgG/M secondary antibody (Jackson Immunoresearch). Arrays were scanned using a laser-based GENEPIX 4000B scanner (Molecular Devices) to obtain digital images for each array.

Figure 8:
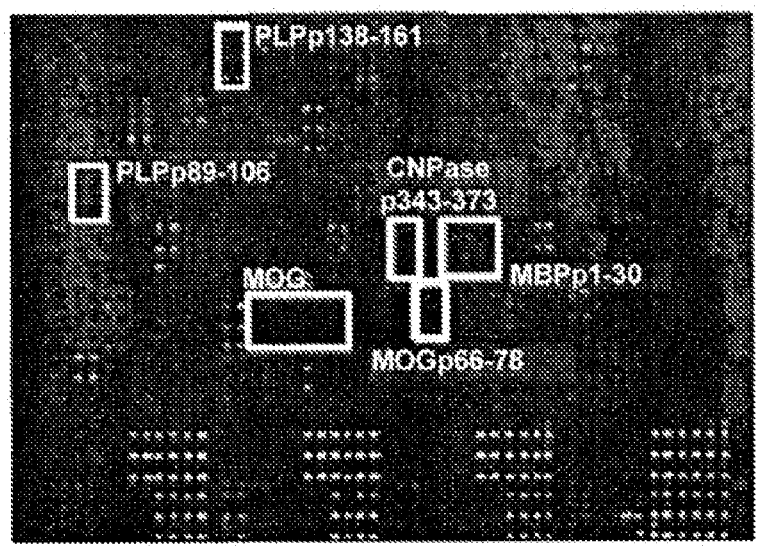
FIGS. 8-10 are fluorescent images of 2304-feature myelin proteome arrays probed with (FIG. 8) normal SJL serum which demonstrated no autoantibody reactivity against myelin proteins, and (FIGS. 9 & 10) serum from mice with chronic relapsing EAE which demonstrate autoantibody reactivity against the inciting PLP peptide (yellow rectangle), and spreading of the B cell response to involve adjacent PLP epitopes and 3 additional myelin proteins (MBP, CNPase, and MOG).
Figure 9:
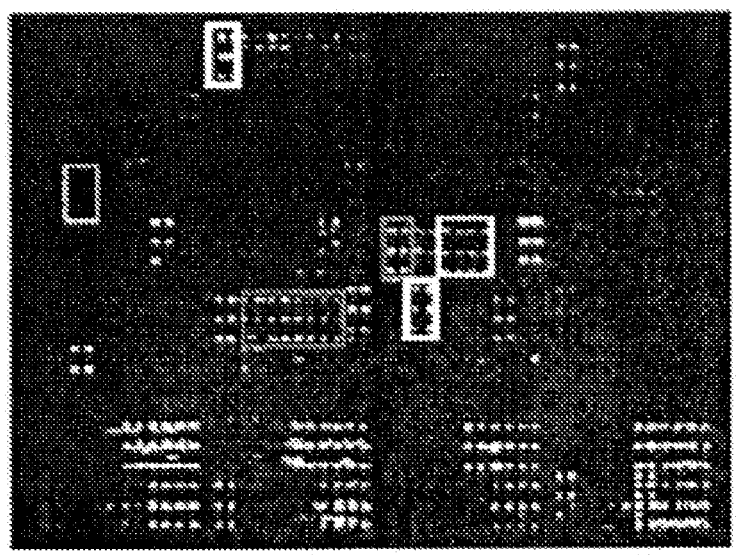
Figure 10:
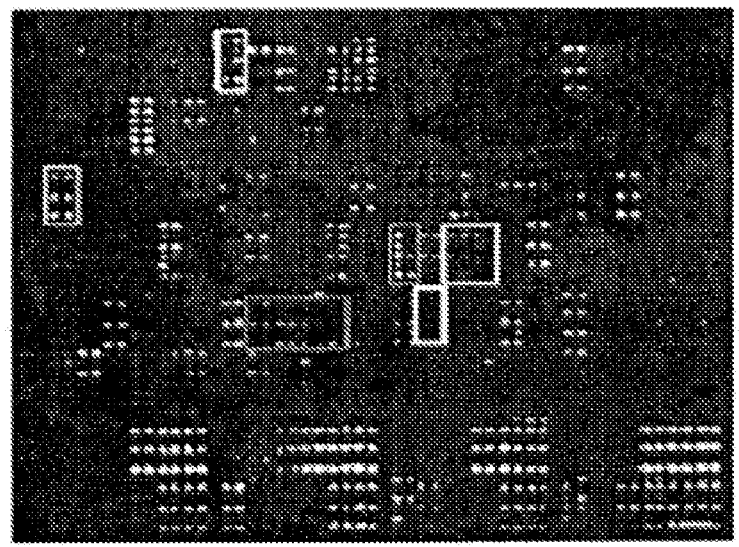

FIGS. 8-10 provide an example of autoantibody reactivity in sera derived from mice with autoimmune encephalomyelitis (EAE), and mouse model of autoimmune demyelination. 2304-feature myelin proteome arrays were produced using a robotic arrayer to attach 485 distinct myelin peptides and proteins to the surface of poly-L-lysine-coated slides in an ordered array. Individual arrays were probed with (FIG. 8) normal SJL serum, which demonstrated no autoantibody reactivity against myelin proteins, and (FIGS. 9 and 10) serum from mice with chronic relapsing EAE, which demonstrated autoantibody reactivity against the inciting PLP peptide (yellow rectangle), and spreading of the B cell response to involve adjacent PLP epitopes and 3 additional myelin proteins (MBP, CNPase, and MOG). Bound antibodies were detected using Cy-3-conjugated goat-anti-mouse IgM/IgG prior to scanning with a GENEPIX 4000B scanner (Molecular Devices). See Robinson et al., Nat. Biotechnol., 2003; 21(9):1033-9.

Data Analysis

Scanned images of arrays were analyzed using GENEPIX 5.0 Pro software (Molecular Devices) to determine the fluorescence intensity at each antigen feature. Data were analyzed with software programs including Excel, Cluster and Tree View software (Eisen et al., Proc. Natl. Acad. Sci. U.S.A., 1998; 95(25):14863-8), Significant Analysis of Microarrays (SAM; Tusher et al., Proc. Natl. Acad. Sci. U.S.A., 1997; 98(18):10515), and Predictive Analysis of Microarrays (PAM; Tibshirani et al., Proc. Natl. Acad. Sci. U.S. A., 2002; 99(10):6567-72). SAM was applied to identify autoantibody reactivities that are statistically associated with ADEM. PAM performs sample classification from RNA transcript data to provide a list of significant autoantibodies whose expression characterizes each sample group, and for the described studies autoantibodies that characterize ADEM.

Results

Figure 11:
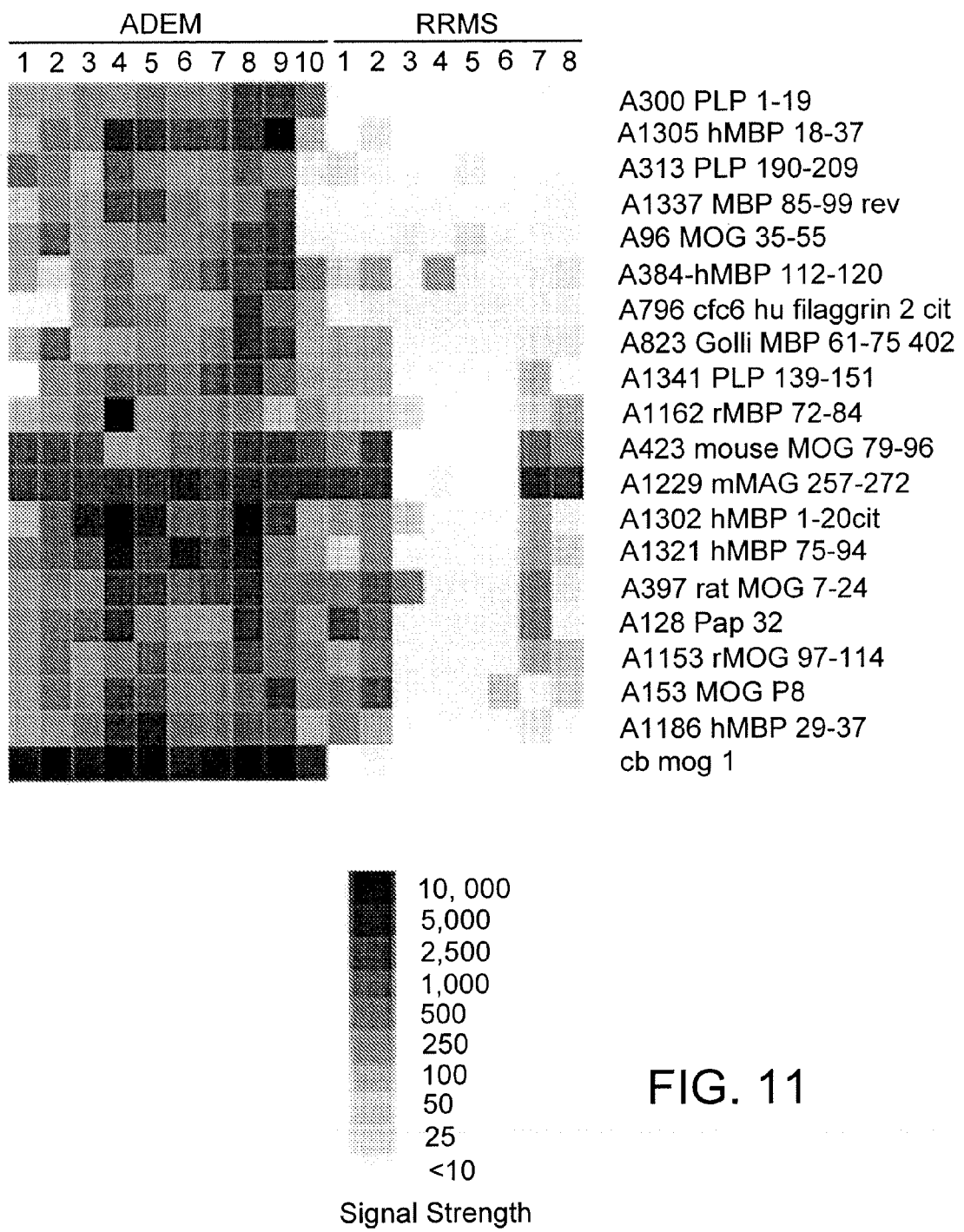
FIG. 11 is a false-colored image of the results of SAM applied to identify autoantibody reactivities with statistically-significant differences between ADEM and RRMS controls. Out of the total of 300+ myelin proteins and peptides included on myelin arrays, SAM identified the displayed list as exhibiting statistically increased reactivity in ADEM (false discovery rate 2.3%, fold change>3). ADEM and MS patients, as well as the SAM-identified antigen features, were arranged with Cluster and displayed with TreeView software. The ADEM patients cluster together and exhibit statistically significant increased autoantibody reactivity against the displayed epitopes as compared to the RRMS controls.
Figure 12:
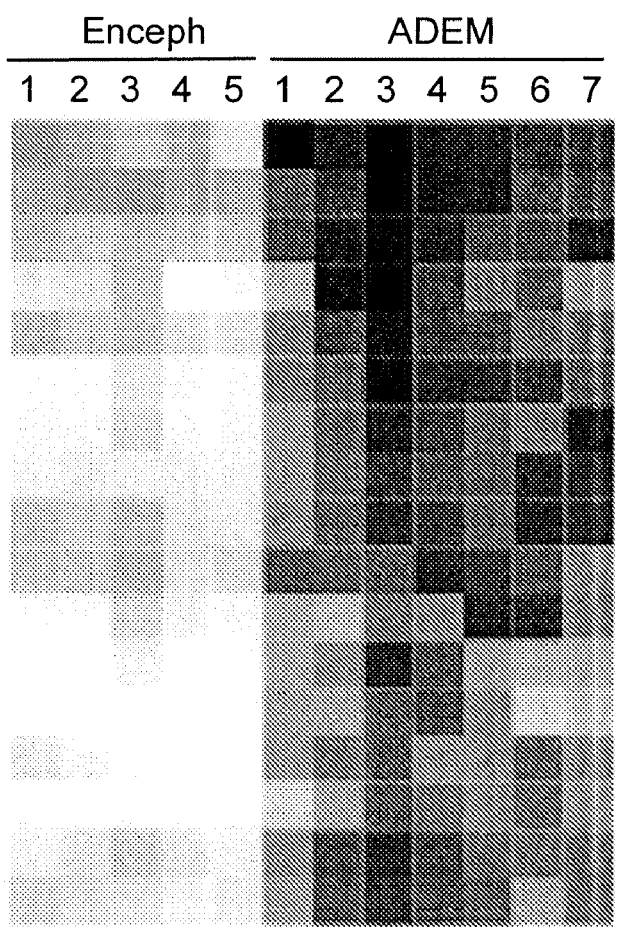
FIG. 12 is a false-colored image of the results of SAM applied to identify autoantibody reactivities with statistically-significant differences between ADEM and viral encephalitis controls. Analysis and display were performed using methods analogous to those described in FIG. 11. The ADEM patients cluster together and exhibit statistically significant increased autoantibody reactivity against the displayed epitopes as compared to the viral encephalitis controls.

Myelin arrays were applied to profile autoantibody responses in ADEM, MS and other neurologic diseases. FIG. 11 is a representative cluster of Montreal ADEM vs. relapsing-remitting MS (RRMS). This figure was generated by using SAM to identify antigen features with statistically significant differences between array reactivity in ADEM samples as compared to adult RRMS samples. Out of the total of 300+ myelin proteins and peptides included on myelin arrays SAM identified the displayed list as exhibiting statistically increased reactivity in ADEM (fold change>3). The false discovery rate is 2.3% for these individual antigen hits. A similar analysis was performed to compare autoantibody reactivity in samples derived from ADEM and viral encephalitis. Clustering illustrates that the ADEM samples possess significantly higher antibody reactivity against a panel of myelin epitopes when compared to samples derived from patients with RRMS and viral encephalitis.

Predictive Analysis of Microarray (PAM) was further used to identify anti-myelin autoantibody reactivity profiles that differentiate ADEM from RRMS. PAM was trained on a dataset generated from myelin array profiling of ADEM (from Germany and the UK) and MS patient sera, and PAM identified a set of MBP, MOG and MOBP peptides as differentiating ADEM from RRMS. The predictive value of this set of autoantibodies was then tested on myelin array results from an independent set of ADEM (from Boston and Montreal) and RRMS (from Japan) samples, PAM predicted 24/32 ADEM and 15/18 RRMS correctly.

TABLE 4

List of Significant Auto-Antigens Associated with ADEM

| Antigen | Sequence | SEQ ID NO: |
|---|---|---|
| hMBP 80-102 | TQDENPVVHFFKNIVTPRTPPPS | 17 |
| rMBP 10-20 | HGSKYLATAST | 18 |
| MBP 9-20 Ac | QRHGSKYLATAS | 19 |
| hMOBP 51-70 | CFYQKKEEDWICCACQKTRT | 20 |
| MBP 85-99 | PVVHFFKNIVTPRTP | 21 |
| rMOG 7-24 | GPGHPIRALVGDEAELPC | 22 |
| MOG P15 | Recombinant protein encoding the extracellular Ig domain of MOG: VELPCRISPGKNATGMEVGWYRPPFSRVVHLYRNG KDQDGDQAPEYRGRTELLKDAIGEGKVTLRIRNVRFSDEGGFTCFF | 23 |
| rMOG 25-42 | RISPGKNATGMEVGWYRS | 24 |
| mMOG 79-96 | GKVALRIQNVRFSDEGGY | 25 |
| hMBP 20-28 | TMDHARHGF | 26 |
| hMBP 29-37 | LPRHRDTGI | 8 |
| hMBP 1-20 | ASQKRPSQRHGSKYLATAST | 15 |

MBP sequences are derived from myelin basic protein isoform 1"

/protein_id = "NP_001020252.1"

/db_xref = "GI: 68509930"

/db_xref = "GeneID: 4155"

/db_xref = "HGNC: 6925"

/db_xref = "MIM: 159430"

MOBP sequencesare derived from

LOCUS      BAA05660 183 aa linear PRI 06-FEB-1999

DEFINITION  MOBP [Homo sapiens].

ACCESSION   BAA05660

VERSION     BAA05660.1 GI: 1408050

DBSOURCE    locus HUMBP2 accession D28114.1

TABLE 4-continued

MOG sequences are derived from:

LOCUS      AAH35938  295 aa  linear  PRI  21-JUL-2005

DEFINITION  MOG protein [Homo sapiens].

ACCESSION  AAH35938

VERSION    AAH35938.1 GI: 23270927

DBSOURCE   accession BC035938.1

KEYWORDS   MGC.

SOURCE     Homo sapiens (human)

These results indicate that the presence of autoantibodies to the antigens listed in Table 4 can be used to diagnose ADEM, and to rule out RRMS and viral encephalitis, with great accuracy.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting the presence of autoantibodies to myelin oligodendrocyte glycoprotein (MOG) in a subject, the method comprising:
   obtaining a sample comprising serum or CSF from the subject;
   contacting the sample with a multimeric polypeptide, wherein the multimeric polypeptide comprises two or more fusion polypeptides comprising
      (i) a first portion comprising an antigenic extracellular domain of MOG comprising the sequence RISPGKNATGMEVGWYRS (SEQ ID NO:24); and
      (ii) a second portion comprising a multimerizing domain linked to the first portion, optionally via a linker,
   under conditions that allow binding of the multimeric polypeptide to antibodies present in the sample, if any, to thereby form multimeric polypeptide/antibody complexes; and
      detecting the presence of said multimeric polypeptide/antibody complexes in the sample, wherein the presence of multimeric polypeptide/antibody complexes in the sample indicates the presence of autoantibodies to MOG in the subject.

2. The method of claim 1, further comprising selecting or rejecting the subject for inclusion in a clinical trial based upon the presence or absence of MOG autoantibodies in the sample.

3. A method of detecting the presence of antibodies to myelin oligodendrocyte glycoprotein (MOG) in a sample, the method comprising:
   contacting the sample with a tetrameric polypeptide,
   wherein the tetrameric polypeptide comprises four fusion polypeptides comprising
      (i) a first portion comprising an antigenic extracellular domain of MOG comprising the sequence RISPGKNATGMEVGWYRS (SEQ ID NO:24); and
      (ii) a second portion comprising a multimerizing domain linked to the first portion, optionally via a linker,
   under conditions that allow binding of the tetrameric polypeptide to antibodies present in the sample, if any, to form tetrameric polypeptide/antibody complexes; and
      detecting the presence of tetrameric polypeptide/antibody complexes in the sample, thereby detecting the presence of the antibody in the sample.

4. The method of claim 1, wherein the multimerizing domain comprises streptavidin.

5. The method of claim 1, wherein the multimeric polypeptide further comprises a linker.

6. The method of claim 1, wherein the multimeric polypeptide is a tetramer.

7. The method of claim 3, wherein the multimerizing domain comprises streptavidin.

8. The method of claim 3, wherein the multimeric polypeptide further comprises a linker.

9. A method of detecting the presence of autoantibodies to myelin oligodendrocyte glycoprotein (MOG) in a subject, the method comprising:
   obtaining a sample comprising serum or CSF from the subject;
   contacting the sample with a multimeric polypeptide, wherein the multimeric polypeptide comprises two or more fusion polypeptides comprising
      (i) a first portion comprising an antigenic extracellular domain of MOG comprising amino acids 27-146 of SEQ ID NO:2; and
      (ii) a second portion comprising a multimerizing domain linked to the first portion, optionally via a linker,
   under conditions that allow binding of the multimeric polypeptide to antibodies present in the sample, if any, to thereby form multimeric polypeptide/antibody complexes; and
      detecting the presence of said multimeric polypeptide/antibody complexes in the sample, wherein the presence of multimeric polypeptide/antibody complexes in the sample indicates the presence of autoantibodies to MOG in the subject.

10. A method of detecting the presence of antibodies to myelin oligodendrocyte glycoprotein (MOG) in a sample, the method comprising:
   contacting the sample with a tetrameric polypeptide,
   wherein the tetrameric polypeptide comprises four fusion polypeptides comprising
      (i) a first portion comprising an antigenic extracellular domain of MOG comprising amino acids 27-146 of SEQ ID NO: 2; and
      (ii) a second portion comprising a multimerizing domain linked to the first portion, optionally via a linker,
   under conditions that allow binding of the tetrameric polypeptide to antibodies present in the sample, if any, to form tetrameric polypeptide/antibody complexes; and
      detecting the presence of tetrameric polypeptide/antibody complexes in the sample,
      thereby detecting the presence of the antibody in the sample.

11. The method of claim 9, wherein the multimerizing domain comprises streptavidin.

12. The method of claim 9, wherein the multimeric polypeptide further comprises a linker.

13. The method of claim 9, wherein the multimeric polypeptide is a tetramer.

14. The method of claim 10, wherein the multimerizing domain comprises streptavidin.

15. The method of claim 10, wherein the multimeric polypeptide further comprises a linker.

* * * * *

SEQUENCE LISTING

<160> NUMBER OF SEQ ID NOS: 26

<210> SEQ ID NO 1
<211> LENGTH: 881
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (16)...(852)

<400> SEQUENCE: 1

```
aagcttgccg ccacc atg gta ccg tgc acg ctg ctc ctg ttg gcg gcc         51
               Met Val Pro Cys Thr Leu Leu Leu Leu Ala Ala
               1               5                   10 gcc ctg gct ccg act cag acc cgc gcg cag ttc aga gtg ata gga cca       99
Ala Leu Ala Pro Thr Gln Thr Arg Ala Gln Phe Arg Val Ile Gly Pro
            15                  20                  25 aga cac cct atc cgg gct ctg gtc ggg gat gaa gtg gaa ttg cca tgt      147
Arg His Pro Ile Arg Ala Leu Val Gly Asp Glu Val Glu Leu Pro Cys
        30                  35                  40 cgc ata tct cct ggg aag aac gct aca ggc atg gag gtg ggg tgg tac      195
Arg Ile Ser Pro Gly Lys Asn Ala Thr Gly Met Glu Val Gly Trp Tyr
45                  50                  55                  60 cgc ccc ccc ttc tct agg gtg gtt cat ctc tac aga aat ggc aag gac      243
Arg Pro Pro Phe Ser Arg Val Val His Leu Tyr Arg Asn Gly Lys Asp
                65                  70                  75 caa gat gga gac cag gca cct gaa tat cgg ggc cgg aca gag ctg ctg      291
Gln Asp Gly Asp Gln Ala Pro Glu Tyr Arg Gly Arg Thr Glu Leu Leu
            80                  85                  90
```

```
aaa gat gct att ggt gag gga aag gtg act ctc agg atc cgg aat gta    339
Lys Asp Ala Ile Gly Glu Gly Lys Val Thr Leu Arg Ile Arg Asn Val
         95                 100                 105 agg ttc tca gat gaa gga ggt ttc acc tgc ttc ttc cga gat cat tct    387
Arg Phe Ser Asp Glu Gly Gly Phe Thr Cys Phe Phe Arg Asp His Ser
    110                 115                 120 tac caa gag gag gca gca atg gaa ttg aaa gta gaa gat cct ttc tac    435
Tyr Gln Glu Glu Ala Ala Met Glu Leu Lys Val Glu Asp Pro Phe Tyr
125                 130                 135                 140 tgg gga tcc ggc atg ggc atg ggc atg atg gcg gaa gcg ggc            483
Trp Gly Ser Gly Met Gly Met Gly Met Met Ala Glu Ala Gly
                145                 150                 155 atc acc ggc acc tgg tat aac cag ctg ggc agc acc ttc atc gtg acc    531
Ile Thr Gly Thr Trp Tyr Asn Gln Leu Gly Ser Thr Phe Ile Val Thr
                160                 165                 170 gcg ggc gcg gat ggc gcg ctg acc ggc acc tat gaa agc gcg gtg ggc    579
Ala Gly Ala Asp Gly Ala Leu Thr Gly Thr Tyr Glu Ser Ala Val Gly
            175                 180                 185 aac gcg gaa agc cgc tat gtg ctg acc ggc cgc tat gat agc gcg ccg    627
Asn Ala Glu Ser Arg Tyr Val Leu Thr Gly Arg Tyr Asp Ser Ala Pro
        190                 195                 200 gcg acc gat ggc agc ggt acc gcg ctg ggc tgg acc gtg gcg tgg aaa    675
Ala Thr Asp Gly Ser Gly Thr Ala Leu Gly Trp Thr Val Ala Trp Lys
205                 210                 215                 220 aac aac tat cgc aac gcg cat agc gcg acc acc tgg agc ggc cag tat    723
Asn Asn Tyr Arg Asn Ala His Ser Ala Thr Thr Trp Ser Gly Gln Tyr
                225                 230                 235 gtg ggc ggc gcg gaa gcg cgc atc aac acc cag tgg ctg ctg acc agc    771
Val Gly Gly Ala Glu Ala Arg Ile Asn Thr Gln Trp Leu Leu Thr Ser
                240                 245                 250 ggc acc acc gaa gcg aac gcg tgg aaa agc acc ctg gtg ggc cat gat    819
Gly Thr Thr Glu Ala Asn Ala Trp Lys Ser Thr Leu Val Gly His Asp
            255                 260                 265 acc ttc acc aaa gtg aaa ccg agc gcg gcg agc tgaaaaaaaa aaaaaaaaaa  872
Thr Phe Thr Lys Val Lys Pro Ser Ala Ala Ser
        270                 275 aaaaagctt                                                          881

<210> SEQ ID NO 2
<211> LENGTH: 279
<212> TYPE: PRT
<213> ORGANISM: Artificial Sequence
<220> FEATURE:
<223> OTHER INFORMATION: Synthetic construct

<400> SEQUENCE: 2

Met Val Pro Cys Thr Leu Leu Leu Leu Ala Ala Leu Ala Pro
 1               5                  10                  15

Thr Gln Thr Arg Ala Gln Phe Arg Val Ile Gly Pro Arg His Pro Ile
            20                  25                  30

Arg Ala Leu Val Gly Asp Glu Val Glu Leu Pro Cys Arg Ile Ser Pro
        35                  40                  45

Gly Lys Asn Ala Thr Gly Met Glu Val Gly Trp Tyr Arg Pro Pro Phe
    50                  55                  60

Ser Arg Val Val His Leu Tyr Arg Asn Gly Lys Asp Gln Asp Gly Asp
65                  70                  75                  80

Gln Ala Pro Glu Tyr Arg Gly Arg Thr Glu Leu Leu Lys Asp Ala Ile
                85                  90                  95

Gly Glu Gly Lys Val Thr Leu Arg Ile Arg Asn Val Arg Phe Ser Asp
```

```
                100                 105                 110
Glu Gly Gly Phe Thr Cys Phe Phe Arg Asp His Ser Tyr Gln Glu Glu
            115                 120                 125

Ala Ala Met Glu Leu Lys Val Glu Asp Pro Phe Tyr Trp Gly Ser Gly
    130                 135                 140

Met Gly Met Gly Met Gly Met Met Ala Glu Ala Gly Ile Thr Gly Thr
145                 150                 155                 160

Trp Tyr Asn Gln Leu Gly Ser Thr Phe Ile Val Thr Ala Gly Ala Asp
                165                 170                 175

Gly Ala Leu Thr Gly Thr Tyr Glu Ser Ala Val Gly Asn Ala Glu Ser
            180                 185                 190

Arg Tyr Val Leu Thr Gly Arg Tyr Asp Ser Ala Pro Ala Thr Asp Gly
    195                 200                 205

Ser Gly Thr Ala Leu Gly Trp Thr Val Ala Trp Lys Asn Asn Tyr Arg
210                 215                 220

Asn Ala His Ser Ala Thr Thr Trp Ser Gly Gln Tyr Val Gly Gly Ala
225                 230                 235                 240

Glu Ala Arg Ile Asn Thr Gln Trp Leu Leu Thr Ser Gly Thr Thr Glu
                245                 250                 255

Ala Asn Ala Trp Lys Ser Thr Leu Val Gly His Asp Thr Phe Thr Lys
            260                 265                 270

Val Lys Pro Ser Ala Ala Ser
            275

<210> SEQ ID NO 3
<211> LENGTH: 890
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (16)...(861)

<400> SEQUENCE: 3
aagcttgccg ccacc atg gta ccg tgc acg ctg ctc ctg ctg ttg gcg gcc        51
                 Met Val Pro Cys Thr Leu Leu Leu Leu Leu Ala Ala
                  1               5                  10 gcc ctg gct ccg act cag acc cgc gcg gcg gaa gcg ggc atc acc ggc         99
Ala Leu Ala Pro Thr Gln Thr Arg Ala Ala Glu Ala Gly Ile Thr Gly
                15                  20                  25 acc tgg tat aac cag ctg ggc agc acc ttc atc gtg acc gcg ggc gcg       147
Thr Trp Tyr Asn Gln Leu Gly Ser Thr Phe Ile Val Thr Ala Gly Ala
        30                  35                  40 gat ggc gcg ctg acc ggc acc tat gaa agc gcg gtg ggc aac gcg gaa       195
Asp Gly Ala Leu Thr Gly Thr Tyr Glu Ser Ala Val Gly Asn Ala Glu
45                  50                  55                  60 agc cgc tat gtg ctg acc ggc cgc tat gat agc gcg ccg gcg acc gat       243
Ser Arg Tyr Val Leu Thr Gly Arg Tyr Asp Ser Ala Pro Ala Thr Asp
                65                  70                  75 ggc agc ggt acc gcg ctg ggc tgg acc gtg gcg tgg aaa aac aac tat       291
Gly Ser Gly Thr Ala Leu Gly Trp Thr Val Ala Trp Lys Asn Asn Tyr
            80                  85                  90 cgc aac gcg cat agc gcg acc acc tgg agc ggc cag tat gtg ggc ggc       339
Arg Asn Ala His Ser Ala Thr Thr Trp Ser Gly Gln Tyr Val Gly Gly
        95                 100                 105 gcg gaa gcg cgc atc aac acc cag tgg ctg ctg acc agc ggc acc acc       387
Ala Glu Ala Arg Ile Asn Thr Gln Trp Leu Leu Thr Ser Gly Thr Thr
    110                 115                 120
```

```
gaa gcg aac gcg tgg aaa agc acc ctg gtg ggc cat gat acc ttc acc        435
Glu Ala Asn Ala Trp Lys Ser Thr Leu Val Gly His Asp Thr Phe Thr
125                 130                 135                 140 aaa gtg aaa ccg agc gcg gcg agc gga tcc ggc atg ggc atg ggc atg        483
Lys Val Lys Pro Ser Ala Ala Ser Gly Ser Gly Met Gly Met Gly Met
                145                 150                 155 ggc atg atg ggc ggc gga cag ttc aga gtg ata gga cca aga cac cct        531
Gly Met Met Gly Gly Gly Gln Phe Arg Val Ile Gly Pro Arg His Pro
            160                 165                 170 atc cgg gct ctg gtc ggg gat gaa gtg gaa ttg cca tgt cgc ata tct        579
Ile Arg Ala Leu Val Gly Asp Glu Val Glu Leu Pro Cys Arg Ile Ser
        175                 180                 185 cct ggg aag aac gct aca ggc atg gag gtg ggg tgg tac cgc ccc ccc        627
Pro Gly Lys Asn Ala Thr Gly Met Glu Val Gly Trp Tyr Arg Pro Pro
    190                 195                 200 ttc tct agg gtg gtt cat ctc tac aga aat ggc aag gac caa gat gga        675
Phe Ser Arg Val Val His Leu Tyr Arg Asn Gly Lys Asp Gln Asp Gly
205                 210                 215                 220 gac cag gca cct gaa tat cgg ggc cgg aca gag ctg ctg aaa gat gct        723
Asp Gln Ala Pro Glu Tyr Arg Gly Arg Thr Glu Leu Leu Lys Asp Ala
                225                 230                 235 att ggt gag gga aag gtg act ctc agg atc cgg aat gta agg ttc tca        771
Ile Gly Glu Gly Lys Val Thr Leu Arg Ile Arg Asn Val Arg Phe Ser
            240                 245                 250 gat gaa gga ggt ttc acc tgc ttc ttc cga gat cat tct tac caa gag        819
Asp Glu Gly Gly Phe Thr Cys Phe Phe Arg Asp His Ser Tyr Gln Glu
        255                 260                 265 gag gca gca atg gaa ttg aaa gta gaa gat cct ttc tac tgg                861
Glu Ala Ala Met Glu Leu Lys Val Glu Asp Pro Phe Tyr Trp
    270                 275                 280 tgaaaaaaaa aaaaaaaaaa aaaaagctt                                        890

<210> SEQ ID NO 4
<211> LENGTH: 282
<212> TYPE: PRT
<213> ORGANISM: Artificial Sequence
<220> FEATURE:
<223> OTHER INFORMATION: Synthetic construct

<400> SEQUENCE: 4

Met Val Pro Cys Thr Leu Leu Leu Leu Ala Ala Leu Ala Pro
1               5                   10                  15

Thr Gln Thr Arg Ala Ala Glu Ala Gly Ile Thr Gly Thr Trp Tyr Asn
                20                  25                  30

Gln Leu Gly Ser Thr Phe Ile Val Thr Ala Gly Ala Asp Gly Ala Leu
            35                  40                  45

Thr Gly Thr Tyr Glu Ser Ala Val Gly Asn Ala Glu Ser Arg Tyr Val
        50                  55                  60

Leu Thr Gly Arg Tyr Asp Ser Ala Pro Ala Thr Asp Gly Ser Gly Thr
65                  70                  75                  80

Ala Leu Gly Trp Thr Val Ala Trp Lys Asn Asn Tyr Arg Asn Ala His
                85                  90                  95

Ser Ala Thr Thr Trp Ser Gly Gln Tyr Val Gly Gly Ala Glu Ala Arg
            100                 105                 110

Ile Asn Thr Gln Trp Leu Leu Thr Ser Gly Thr Glu Ala Asn Ala
        115                 120                 125

Trp Lys Ser Thr Leu Val Gly His Asp Thr Phe Thr Lys Val Lys Pro
    130                 135                 140

Ser Ala Ala Ser Gly Ser Gly Met Gly Met Gly Met Gly Met Met Gly
```

```
                    145                 150                 155                 160
Gly Gly Gln Phe Arg Val Ile Gly Pro Arg His Pro Ile Arg Ala Leu
                165                 170                 175

Val Gly Asp Glu Val Glu Leu Pro Cys Arg Ile Ser Pro Gly Lys Asn
            180                 185                 190

Ala Thr Gly Met Glu Val Gly Trp Tyr Arg Pro Pro Phe Ser Arg Val
        195                 200                 205

Val His Leu Tyr Arg Asn Gly Lys Asp Gln Asp Gly Asp Gln Ala Pro
    210                 215                 220

Glu Tyr Arg Gly Arg Thr Glu Leu Leu Lys Asp Ala Ile Gly Glu Gly
225                 230                 235                 240

Lys Val Thr Leu Arg Ile Arg Asn Val Arg Phe Ser Asp Glu Gly Gly
                245                 250                 255

Phe Thr Cys Phe Phe Arg Asp His Ser Tyr Gln Glu Glu Ala Ala Met
            260                 265                 270

Glu Leu Lys Val Glu Asp Pro Phe Tyr Trp
        275                 280

<210> SEQ ID NO 5
<211> LENGTH: 500
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (16)...(471)

<400> SEQUENCE: 5
aagcttgccg ccacc atg gta ccg tgc acg ctg ctc ctg ctg ttg gcg gcc       51
                Met Val Pro Cys Thr Leu Leu Leu Leu Leu Ala Ala
                  1               5                  10 gcc ctg gct ccg act cag acc cgc gcg cag ttc aga gtg ata gga cca       99
Ala Leu Ala Pro Thr Gln Thr Arg Ala Gln Phe Arg Val Ile Gly Pro
         15                  20                  25 aga cac cct atc cgg gct ctg gtc ggg gat gaa gtg gaa ttg cca tgt      147
Arg His Pro Ile Arg Ala Leu Val Gly Asp Glu Val Glu Leu Pro Cys
 30                  35                  40 cgc ata tct cct ggg aag aac gct aca ggc atg gag gtg ggg tgg tac      195
Arg Ile Ser Pro Gly Lys Asn Ala Thr Gly Met Glu Val Gly Trp Tyr
45                  50                  55                  60 cgc ccc ccc ttc tct agg gtg gtt cat ctc tac aga aat ggc aag gac      243
Arg Pro Pro Phe Ser Arg Val Val His Leu Tyr Arg Asn Gly Lys Asp
                 65                  70                  75 caa gat gga gac cag gca cct gaa tat cgg ggc cgg aca gag ctg ctg      291
Gln Asp Gly Asp Gln Ala Pro Glu Tyr Arg Gly Arg Thr Glu Leu Leu
             80                  85                  90 aaa gat gct att ggt gag gga aag gtg act ctc agg atc cgg aat gta      339
Lys Asp Ala Ile Gly Glu Gly Lys Val Thr Leu Arg Ile Arg Asn Val
         95                 100                 105 agg ttc tca gat gaa gga ggt ttc acc tgc ttc ttc cga gat cat tct      387
Arg Phe Ser Asp Glu Gly Gly Phe Thr Cys Phe Phe Arg Asp His Ser
110                 115                 120 tac caa gag gag gca gca atg gaa ttg aaa gta gaa gat cct ttc tac      435
Tyr Gln Glu Glu Ala Ala Met Glu Leu Lys Val Glu Asp Pro Phe Tyr
125                 130                 135                 140 tgg gga tcc ggc atg ggc atg ggc atg ggc atg atg tgaaaaaaaa           481
Trp Gly Ser Gly Met Gly Met Gly Met Gly Met Met
                145                 150 aaaaaaaaaa aaaagctt                                                  500
```

<210> SEQ ID NO 6
<211> LENGTH: 152
<212> TYPE: PRT
<213> ORGANISM: Artificial Sequence
<220> FEATURE:
<223> OTHER INFORMATION: Synthetic construct

<400> SEQUENCE: 6

```
Met Val Pro Cys Thr Leu Leu Leu Leu Ala Ala Leu Ala Pro
 1               5                  10                  15

Thr Gln Thr Arg Ala Gln Phe Arg Val Ile Gly Pro Arg His Pro Ile
            20                  25                  30

Arg Ala Leu Val Gly Asp Glu Val Glu Leu Pro Cys Arg Ile Ser Pro
                35                  40                  45

Gly Lys Asn Ala Thr Gly Met Glu Val Gly Trp Tyr Arg Pro Pro Phe
     50                  55                  60

Ser Arg Val Val His Leu Tyr Arg Asn Gly Lys Asp Gln Asp Gly Asp
 65                  70                  75                  80

Gln Ala Pro Glu Tyr Arg Gly Arg Thr Glu Leu Leu Lys Asp Ala Ile
                 85                  90                  95

Gly Glu Gly Lys Val Thr Leu Arg Ile Arg Asn Val Arg Phe Ser Asp
                100                 105                 110

Glu Gly Gly Phe Thr Cys Phe Phe Arg Asp His Ser Tyr Gln Glu Glu
            115                 120                 125

Ala Ala Met Glu Leu Lys Val Glu Asp Pro Phe Tyr Trp Gly Ser Gly
    130                 135                 140

Met Gly Met Gly Met Gly Met Met
145                 150
```

<210> SEQ ID NO 7
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 7

```
Gly Ser Gly Met Gly Met Gly Met Gly Met Met
 1               5                  10
```

<210> SEQ ID NO 8
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 8

```
Leu Pro Arg His Arg Asp Thr Gly Ile
 1               5
```

<210> SEQ ID NO 9
<211> LENGTH: 60
<212> TYPE: DNA
<213> ORGANISM: Artificial Sequence
<220> FEATURE:
<223> OTHER INFORMATION: Synthetically generated oligonucleotide

<400> SEQUENCE: 9
tgttggcggc cgccctggct ccgactcaga cccgcgcgca gttcagagtg ataggaccaa    60

<210> SEQ ID NO 10
<211> LENGTH: 72
<212> TYPE: DNA
<213> ORGANISM: Artificial Sequence
<220> FEATURE:
<223> OTHER INFORMATION: Synthetically generated oligonucleotide

<400> SEQUENCE: 10
ggtgatgccc gcttccgcca tcatgcccat gcccatgccc atgccggatc cccagtagaa    60
aggatcttct ac                                                        72

<210> SEQ ID NO 11
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 11
atggcggaag cgggcatcac c                                              21

<210> SEQ ID NO 12
<211> LENGTH: 55
<212> TYPE: DNA
<213> ORGANISM: Artificial Sequence
<220> FEATURE:
<223> OTHER INFORMATION: Synthetically generated oligonucleotide

<400> SEQUENCE: 12
aaaaaaaagc ttttttttt ttttttttt tttcagctcg ccgcgctcgg tttca          55

<210> SEQ ID NO 13
<211> LENGTH: 55
<212> TYPE: DNA
<213> ORGANISM: Artificial Sequence
<220> FEATURE:
<223> OTHER INFORMATION: Synthetically generated oligonucleotide

<400> SEQUENCE: 13
aaaaaaaagc ttttttttt ttttttttt tttcagctcg ccgcgctcgg tttca          55

<210> SEQ ID NO 14
<211> LENGTH: 60
<212> TYPE: DNA
<213> ORGANISM: Artificial Sequence
<220> FEATURE:
<223> OTHER INFORMATION: Synthetically generated oligonucleotide

<400> SEQUENCE: 14
tgttggcggc cgccctggct ccgactcaga cccgcgcggc ggaagcgggc atcaccggca    60

<210> SEQ ID NO 15
<211> LENGTH: 20
<212> TYPE: PRT
<213> ORGANISM: Artificial Sequence
<220> FEATURE:
<223> OTHER INFORMATION: synthetically generated peptide

<400> SEQUENCE: 15

Ala Ser Gln Lys Arg Pro Ser Gln Arg His Gly Ser Lys Tyr Leu Ala
 1               5                  10                  15

Thr Ala Ser Thr
            20

<210> SEQ ID NO 16
<211> LENGTH: 55

-continued

```
<212> TYPE: DNA
<213> ORGANISM: Artificial Sequence
<220> FEATURE:
<223> OTHER INFORMATION: Synthetically generated oligonucleotide

<400> SEQUENCE: 16
aaaaaaagct tttttttttt tttttttttt ttcacatcat gcccatgccc atgcc          55

<210> SEQ ID NO 17
<211> LENGTH: 23
<212> TYPE: PRT
<213> ORGANISM: Artificial Sequence
<220> FEATURE:
<223> OTHER INFORMATION: Synthetically generated peptide

<400> SEQUENCE: 17

Thr Gln Asp Glu Asn Pro Val Val His Phe Phe Lys Asn Ile Val Thr
1               5                   10                  15

Pro Arg Thr Pro Pro Pro Ser
            20

<210> SEQ ID NO 18
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 18

His Gly Ser Lys Tyr Leu Ala Thr Ala Ser Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 19

Gln Arg His Gly Ser Lys Tyr Leu Ala Thr Ala Ser
1               5                   10

<210> SEQ ID NO 20
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 20

Cys Phe Tyr Gln Lys Lys Glu Glu Asp Trp Ile Cys Cys Ala Cys Gln
1               5                   10                  15

Lys Thr Arg Thr
            20

<210> SEQ ID NO 21
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 21

Pro Val Val His Phe Phe Lys Asn Ile Val Thr Pro Arg Thr Pro
1               5                   10                  15
```

```
<210> SEQ ID NO 22
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 22

Gly Pro Gly His Pro Ile Arg Ala Leu Val Gly Asp Glu Ala Glu Leu
 1               5                  10                  15

Pro Cys

<210> SEQ ID NO 23
<211> LENGTH: 81
<212> TYPE: PRT
<213> ORGANISM: Artificial Sequence
<220> FEATURE:
<223> OTHER INFORMATION: Synthetically generated peptide

<400> SEQUENCE: 23

Val Glu Leu Pro Cys Arg Ile Ser Pro Gly Lys Asn Ala Thr Gly Met
 1               5                  10                  15

Glu Val Gly Trp Tyr Arg Pro Pro Phe Ser Arg Val Val His Leu Tyr
             20                  25                  30

Arg Asn Gly Lys Asp Gln Asp Gly Asp Gln Ala Pro Glu Tyr Arg Gly
         35                  40                  45

Arg Thr Glu Leu Leu Lys Asp Ala Ile Gly Glu Gly Lys Val Thr Leu
     50                  55                  60

Arg Ile Arg Asn Val Arg Phe Ser Asp Glu Gly Gly Phe Thr Cys Phe
 65                  70                  75                  80

Phe

<210> SEQ ID NO 24
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 24

Arg Ile Ser Pro Gly Lys Asn Ala Thr Gly Met Glu Val Gly Trp Tyr
 1               5                  10                  15

Arg Ser

<210> SEQ ID NO 25
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 25

Gly Lys Val Ala Leu Arg Ile Gln Asn Val Arg Phe Ser Asp Glu Gly
 1               5                  10                  15

Gly Tyr

<210> SEQ ID NO 26
<211> LENGTH: 9
<212> TYPE: PRT
<213> ORGANISM: Artificial Sequence
<220> FEATURE:
<223> OTHER INFORMATION: Synthetically generated peptide
```

```
<400> SEQUENCE: 26

Thr Met Asp His Ala Arg His Gly Phe
1               5
```